Figure 1:
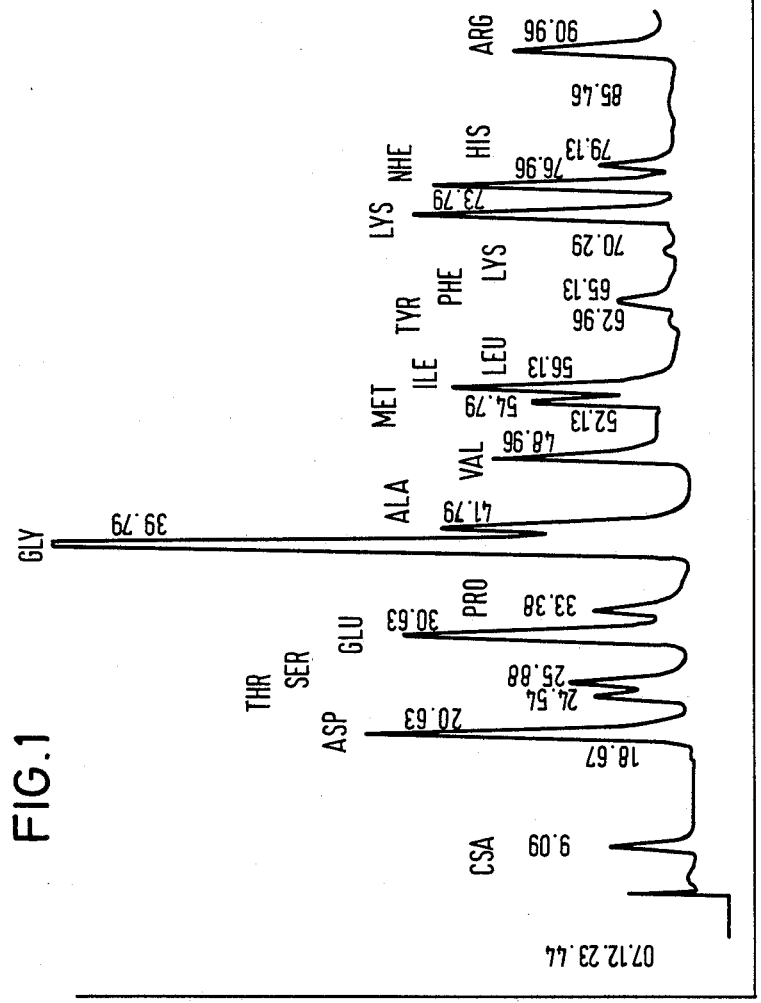

| United States Patent [19] | [11] Patent Number: 4,826,680 |
| Jaeger | [45] Date of Patent: May 2, 1989 |

[54] PHARMACEUTICAL COMPOSITION CONTAINING THYMUS EXTRACT FRACTIONS

[75] Inventor: Karl-Heinz Jaeger, Luzern, Switzerland

[73] Assignee: Dr. Kurt Mulli Nachf. GmbH & Co. KG, Neuenburg, Fed. Rep. of Germany

[21] Appl. No.: 922,001

[22] Filed: Oct. 22, 1986

[30] Foreign Application Priority Data

Oct. 23, 1985 [DE] Fed. Rep. of Germany ....... 3537707

[51] Int. Cl.$^4$ .................. A61K 37/02; A61K 31/525; C07K 7/48
[52] U.S. Cl. ........................................ 424/95; 514/21; 514/251; 530/301; 530/854; 435/69
[58] Field of Search .................... 424/95; 514/21, 251; 530/301, 854; 435/69

[56] References Cited

U.S. PATENT DOCUMENTS 4,374,823 2/1983 Folkers et al. .................. 424/95
4,444,757 4/1984 Strausser .......................... 514/21

OTHER PUBLICATIONS

Goldstein et al., Rec. Prog. Hormone Res., vol. 37, pp. 369–412, 1981.

*Primary Examiner*—Johnnie R. Brown
*Assistant Examiner*—Jacqueline M. Stone
*Attorney, Agent, or Firm*—Felfe & Lynch

[57] ABSTRACT

A pharmaceutical composition is described, which contains a fraction consisting of low molecular proteins and/or oligo peptides, and a yellow fraction containing riboflavine, which is associated with organ specific oligo peptides, which fractions are obtainable by fractionation of thymus extract. This composition has a significant immuno stimulating activity, and can be used for the treatment of immuno deficiency diseases, as for example, for T-cell-deficiencies.

17 Claims, 7 Drawing Sheets

PHARMACEUTICAL COMPOSITION CONTAINING THYMUS EXTRACT FRACTIONS

The invention relates to a pharmaceutical composition containing thymus extract fractions.

It is known, that the immunologic system of the body is regulated by the thymus gland, and that such functions can also be performed by cell-free protein extracts of the thymus gland. Therefore in recent years numerous investigations have been conducted for the preparation, the use and the mechanism of action of thymus tissue extracts (see for instance B. D. Osoba and J. F. A. P. Miller, Nature 199 (1963) 653; A. L. Goldstein and A. White, Contemp. Topics in Immunobiology 1973 339; C. Birr und U. Stollenwerk, Angew. Chemie 91 (1979), 422; Angew. Chemie, Int. Ed. English, 18 (1979) 394). For instance it has been found, that cell-free protein extracts of the thymus gland of calves, as the standard preparation with the name thymosin fraction No. 5, suppress immuno deficiencies in different extent, as a reduced rejection of transplants, an increasing susceptibility to infection, accelerated aging and increased probability of the occurence of tumors. In recent time it has also been reported, that the clinical application of the thymosin fraction No. 5 to patients, which suffered on leukemia or other kinds of cancer, has already shown curative effects, especially with lung cancer (P. B. Chretien et al, J. D. Cancertreat. Report 62 (1978) 1787 to 1790). 977 A. L. Goldstein et al (J. Proc. Natl. Acad. Sci. USA 74 (1977) 725) succeeded in isolating an acid component in pure form from the thymosin-polypeptide-mixture, which has been designated thymosin-$\alpha$1, and for which also the peptide sequence has been determined. With 28 amino acids thymosin-$\alpha$1 has a molecular weight of 3107. Because thymosin-$\alpha$1 can be isolated from thymus glands only very laboriously, methods for its total synthesis have also already been suggested (Journal of American Chemical Society 101, 1 (1979) 253–254; DE-OS No. 29 19 592).

With a molecular weight of 3107 and 28 amino acids thymosin-$\alpha$1 is a relatively large polypeptide, the synthesis of which causes difficulties; although it is known, to use in the immuno therapy thymosin-$\alpha$1-fragments instead of the thymosin-$\alpha$1, which due to their lower molecular weights can be prepared easier, with higher yields and with better purity (cf. DE-OS No. 1 00 974), these fragments display the immuno controlling or immuno stimulating effects only to a smaller extent.

It has now been found, that a mixture of two certain fractions of a thymus tissue extract, namely of a fraction consisting of low molecular weight proteins and/or oligo peptides, and of a yellow fraction containing riboflavin, which is associated with organ specific oligo peptides, has excellent immunological properties, which are comparable with these of the thymosin fraction No. 5 or of thymosin-$\alpha$1, and which are, with respect to the strength of action, even superior. The pharmaceutical compositions according to the present invention are therefore extremely useful for the treatment of immuno deficiency diseases, as of T-cell deficiencies, of accelerated aging, of increased probability of tumor formation, and especially of cancer.

The subject of the present invention is therefore a pharmaceutical composition, containing a fraction consisting of low molecular proteins and/or oligo peptides, and a yellow fraction containing riboflavin, which is associated with organ specific oligo peptides, which fractions are obtainable by fractionation of thymus extract.

Preferably the molecular weight of the low molecular proteins and oligo peptides is <2000 Dalton. In the extract fraction, which contains the riboflavin associated with an organ specific oligo peptide, with "association" a bond can be understood, which for instance is present in the system coenzyme/prosthetic group.

Starting organ for the extracts is thymus, and as the organ donor especially slaughter animals, and particularly calves, are suitable.

Unexpectedly it has also been found, that each one of the two extract fractions, that is the fractions consisting of low molecular protein and/or oligo peptides, or the yellow fraction containing riboflavine, which is associated with organ specific oligo peptides, display a different and/or substantially weaker activities as the composition according to the invention; it is only the combination of the two components, which has the activity according to the present invention.

A marked immune stimulating activity has been found for the composition according to the present invention, which is better than the activity of the known thymosin-fraction No. 5. The product acts as immuno stimulating and thereby shows not only an activity against cancer cells, but has also been proved as of excellent activity against AIDS and severe forms of herpes. This for example results from the fact, that the T-suppressor cells (cytotoxic subpopulation) are intensely increased in proportion to the helper cells.

The thymus extract used as the starting material for the fractionation can be obtained by extraction of thymus in a known manner (cf. for instance B. D. Osoba and J. F. A. P. Miller, Nature 199 (1963) 653; K. H. Jaeger et al, Pharm. Res. Communication 16 (1984) No. 6, 559).

The preparation of the composition according to the present invention can be carried out for example in the following manner: the extract, which has been obtained from the mechanically minced organ by the extraction with water in the presence of external proteases (proteolytic enzymes), as for instance of pancreatin preparations and/or also of papain, which for an intermediate storage optionally is present in form of an aqueous solution, paste or lyophilized, is dissolved in water with stirring, and the aqueous solution, optionally after filtration of turbidities is extracted with phenol; after phase separation (the aqueous phase is discarded) ethanol is added to the phenolic phase, whereby the fraction consisting of low molecular proteins and/or oligo peptides (herein after always designated as peptide fraction) precipitates and is filtrated off; from the filtrate of the precipitation the yellow fraction can be isolated by column chromatography. From the fractions obtained thereby the yellow coloured fractions containing riboflavin, which is associated with organ specific oligo peptides (herein after always designated as yellow fraction or yellow substance) are separated and combined; the other fractions are discarded. The such obtained yellow fraction can be subjected to a further chromatographic separation (exclusion chromatography), for example on a preparative Sephadex ® LH-20-column with water (1% trifluoro ethanol) as eluents; in this case preferably the main fractions obtained at the second chromatographic separation, and especially the fractions containing the yellow component (riboflavin-/oligopeptides) are used as the yellow fraction (yellow substance) of the pharmaceutical composition according to the present invention.

The individual process steps can be carried out in a manner which is known. The chromatographic separation can be carried out under conditions, which are commonly used in an exclusion chromatography (molecular sieve-effect), and with commonly used suitable filling materials (as for example silica gel, Sephadex ®) and elution agents (for example water/1% trifluoro ethanol). The first column chromatography of the filtrate of the phenol-precipitation preferably is carried out on an aluminum oxide column with water as the eluents.

As the water used for the solution of the extract and for the elution preferably water is used, which is bacterial by filtered, sterilized or distilled. It is preferred to carry out the individual process steps under an inert atmosphere, as for example under nitrogen, and the filtration preferably under the conditions of a sterile filtration.

By vacuum drying of the peptide fraction and careful evaporation of the yellow fraction on a rotary evaporator under vacuum or by lyophilization the crystallized, dried products can be obtained; in both cases the drying should be carried out at a temperature $\leq 60°$ C.

The peptide fraction and the yellow fraction can also be used directly as aqueous solution or concentrate, optionally after the addition of further pharmaceutical additives and/or carriers and/or active substances; due to the preparation the solution can still contain small amounts of phenol, but which are not interfering. Especially when preparing concentrates, but also solutions, it can also be expedient, to add stabilizers, for example additional phenol up to a concentration of approximately 0.3 to 1.0 percent by weight, especially 0.5 percent by weight, with respect to the aqueous concentrate or the solution. From the solution it is also possible, for example after an intermediate storage, to isolate the dry substance, for example by lyophilization, which can then be applied per se or together with further active substances and/or pharmaceutical additives and carriers.

Normally the quantitative ratio of the fraction consisting of low molecular proteins and/or oligo peptides (peptide fraction) to the yellow fraction corresponds with the ratio, in which these two components are obtained by the organ extraction and the following separation from the extract; but in some cases, for example for specific applications, it can also be expedient, to use one or the other component in excess or in another quantitative proportion, as the proportion which results directly from the extraction.

As pharmaceutical additives and carriers all such additives and carriers can be used, which are suitable for such an application, whereby the selection is especially dependent from the provided solid or liquid form of application (tablets, dragees, capsules, sirups, solutions, solutions for injection etc.). Also extract-mixtures according to the present invention with one or more additional active substances, which are suitable for the indications, can be used.

The following examples, which refer to preferred embodiments, shall illustrate the invention in more detail, without restricting it. If not otherwise indicated, the preceding and following values of percentage refer to percents by weight, and the temperatures to degree Celsius.

EXAMPLE 1

(a) Chemically pure phenol is used, which corresponds to the purity standards of DAB 7 (7th edition of the German Pharmacopeia); absolute ethanol, which has been denatured by methyl ethyl ketone, is used as ethanol.

An extract obtained from minced thymus of bovine animals is dissolved in water (bacterial filtered) at stirring with a concentration of about 20 weight percent (related to the dry residue). The aqueous solution is preserved with phenol (1 weight percent). After an intermediate storage of 1 to 10 days the aqueous solution is clarified by filtration, and the turbidities filtered off are discarded.

To the clarified filtrate phenol is added and stirring is carried out for about 5 minutes; after the phase separation (approximately 2 to 5 hours) the upper aqueous phase (about 7 weight percent of phenol) is removed and the phenol phase is washed five times with bacterial filtered water (each time during 5 minutes stirring) and afterwards one time with demineralized water. The amounts of phenol dissolving in the wash water are always substituted. The washed phenolic phase is added to ethanol under stirring, whereby the precipitation of the peptides occurs. The residue (peptide fraction) obtained after filtration through filter plates is washed with ethanol, until the phenol content in the washing alcohol is about 1 weight percent. The residue of filtration is dried, after predrying on the filter (vacuum, bacterial filtered air) at a maximum of 60° C. under vacuum.

(b) Physical-chemical characterization of the peptide fraction obtained according to Example 1(a) (hereinafter designated as 101/83)

I. Equipments for assays and results 1.1 Elementary analysis:

The elements carbon, hydrogen and nitrogen are determined gas chromatographically by combustion under a stream of oxygen and subsequent reduction of the nitrogen oxides as carbon dioxide, nitrogen and water. The determination of sulfur is carried out as sulfate by titration with barium perchlorate.

101/83: C 46.52% H 6.92% N 14.3% S 0.83%

1.2 Amino acids analysis:

1.2.1 Content of free amino acids: An assay of 101/83 is investigated quantitatively without any pretreatment for the content of free amino acids using an automatic amino acid analyzer (available from Biotronik) following the method of Stein and Moore. A weighed out sample is dissolved in a certain amount of the starting buffer of the analyzer and an aliquot is injected into the apparatus.

1 mg of the peptide fraction 101/83 contains as free amino acids (n mols): 56.0 cysteine sulfonic acid, 21.6 asparaginic acid, 5.4 serine, 6.0 glutaminic acid, 11.6 proline, 17.8 histidine, about 20 Arg, and 187 and 17.8 nmol of amino acids not definitely identified.

1.2.2 Overall content of amino acids: A weighed-out amount of 101/83 is totally hydrolyzed in concentrated hydrochloric acid/water (1:1) in a bomb tube at 120° C. for 24 hours, then evaporated under vacuum, and the residue is dissolved in a definite amount of the starting buffer (pH =1,8) of the analysator, and an oliquot is injected into the apparatus.

104 μg of the substance 101/83 (peptide fraction from thymus) consists of (n mols): 13,55 cysteine sulfonic acid (2.29 μg), 60.95 asparaginic acid (8.11 μg), 18.1 threonine (2.16 μg), 22.6 serine (2.38 μg), 61.1 glutaminic acid (8.99 μg), 90.3 proline (10.4 μg), 148.1 glycin (11.12 μg), 49.15 alanine (4.38 μg), 37.0 valine (4.33 μg), 25.8 isoleucine (3.38 μg), 36.95 leucine (4.85 μg), 4.4 tyrosine (0,797 μg), 17,55 phenyl alanine (2.9 μg), 36.1 lysine (5.27 μg), 12.65 histidine (1.96 μg), 34.48 arginine (6.0 μg).

Therefore the peptide fraction of thymus corresponds to about 76% of hydrolyzable amino acids (peptidic material; qualitatively nucleotides have been identified by HPLC). The result is shown in FIG. 1.

2.1 Polyacrylamide electrophoresis:

Separating gels of the size $300 \times 150 \times 1$ mm are prepared. Gels of a degree of cross-linking of 10-, 15- and 20% have been used. The separations have been carried out in the presence of sodium dodecycl sulfate (SDS).

For the preparation of the gels the following parent solutions have been used:

| | |
|---|---|
| Lower tris-buffer: | 36,34 tris, 5 ml conc. HCl and 8 ml 10 percent SDS-solution are filled up with water to 200 ml (pH = 8,8). |
| Upper tris-buffer: | 6.06 g tris, 4 ml conc. HCl and 4 ml 10% SDS-solution are filled up with water to 100 ml. |
| Electrophoresis-buffer: | 250 ml reservoir-buffer and 10 ml 10% SDS-solution are filled up to 1000 ml. |
| Reservoir-buffer: | 12.0 tris and 57.6 g glycine are filled up with water to 1000 ml. |
| Acrylamide-solution: | 30 g acrylamide and 0.8 g N,N′—methylene-bis-acrylamide are filled up with water to 100 ml. |
| Ammonium persulfate: | 10% of freshly prepared solution in $H_2O$. |
| Denaturizing-buffer: | Electrophoresis-buffer with 20% glycerol, 3% SDS, 3% mercaptoethanol + brom phenol blue. |
| Fixing bath: | 12,5% TCA |
| Coloring bath: | 2.75 g Coomassie-blue in 500 ml MeOH, 500 ml $H_2O$ and 140 ml AcOH |
| Decoloring bath: | 100 ml MeOH and 150 ml AcOH are filled up with $H_2O$ to 2000 ml. |

| | Separating gel (10%) | Starting gel |
|---|---|---|
| $H_2O$ | 8.33 ml | 3.25 ml |
| upper tris-buffer: | 5.00 | — |
| lower tris-buffer: | — | 1.25 |
| Acrylamide-solution: | 6.67 | 0.55 |
| Tetramethyl ethylene diamine (TEMED): | 0.02 | 0.01 |
| Ammonium sulfate: | 0.01 | 0.02 |

Method of carrying out:

Concentrations of the applied samples: 101/83: 7.5 mg/60 μl

The samples are taken up in 50 μl denaturizing-buffer and 10 μl brom phenol blue-solution. In each case 20 μl are applied.

For the electrophoretic separation the samples are concentrated for the first instance for 45 minutes at 13 mA (max. 400 V) in the area of the collecting gel (starting zone), and are subjected to electrophoresis during 3 hours at constantly 50 mA (8° C. cooling).

Subsequently the gel is removed from the sandwich compartment for development, and is treated for 45 minutes at 22° C. in the coloring bath. Dye stuff in excess is removed in the decoloring bath during 8 hours by repeated changing of the liquid.

Result: As it is to be expected for a peptide preparation, 101/83 cannot be separated electrophoretically in the separate components in 10% crosslinked polyacryl amide-SDS-gel; this indicates the content of low molecular peptides.

2.2 Paper electrophoresis:

In the assay to examine 101/83 with paper electrophoresis, it has been found, that the material under these conditions is not separable in a high voltage field, but gives a broad diffuse band, which shows a color with ninhydrine and which is characteristic for mixed peptides.

Buffer: pH 1,9; composition (ml): glacial acetic acid 15/formic acid 5/water 80 parts per volume.

Paper: Machery, Nagel and Co., MN-chromatographic paper No. 214 (23×58 cm).

The substance sample is dissolved in water/1% trifluoro ethanol and is applied at the starting mark. The separation is carried out at 1000 Volt/2 hours (0° C.). Development: After drying of the electrophoresis papers at 100° C. and spraying with ninhydrine-solution the result of the separation is made visible by heating at 100° /10 min.

3. Determination of the end groups:

The method for marking the end groups with dansyl chloride has been used, which permits in the applied micro technique to indicate N-termini at amino acids, peptides and proteins in the pico-mol range ($10^{-12}$ M) in 2-dimensional, chromatographic separation.

Dansylation: Very small amounts of the substance to be tested are reacted with dansyl chloride in 0.05 mol $NaHCO_3$-buffer, and are subsequently hydrolyzed.

The hydrolysates are investigated with 2-dimensional chromatography on micro-polyamide plates.

1. Dimension, 48% formic acid
2. Dimension, glacial acetic acid/toluene (1:4, v/v).

The N-terminal marked amino acids can be identified and photographed due to their fluorescence in the UV on the polyamide plates. The assignment can be made by the plotting scheme of the dansylated amino acids.

(H. Laatsch, J. Chromatography 173 (1978) 398–402).

Results:

Main marking: Asp, Glu, Gly, Ala, Pro, Arg, His, $NH_4$, $CySO_3H$, Ser.

Background marking: Val, Ile, Leu, Tyr, Phe, Lys.

4. Gel chromatography:

1,455 mg of the peptide fraction from thymus, sample No. 101/83, are separated on a chromatographic column (3×230 cm), Sephadex LH 20, with water (1% trifluoro ethanol) as the eluents.

Fractionation: 20 ml/tube/25 min.

Flow velocity: 0,8 ml/min 2-channel-detection: 1. UV (280 nm), 2. refractometry (sensitivity 32)

Results:

10 main fractions: (9–14), (20), (23), (26), (28), (30–31), (50–55), (60–64), (67–70), (134–148);

8 sub fractions: (15–19), (21–22), (24–25), (27), (29), (32–49), (56–59), (65–66).

Between the tubes 70 and 134 the chromatogram runs along the basis line; these tubes are discarded.

In the additionally carried out thin layer chromatography samples of the main fractions obtained in the gel chromatography are applied.

TLC-plates: silica gel $F_{254}$ (20×20 cm; Merck), layer thickness 0.250 mm.

Solvent: Acetic ester 15/pyridine 20/acetic acid 6/water 11 parts per volume.

Figure 2:
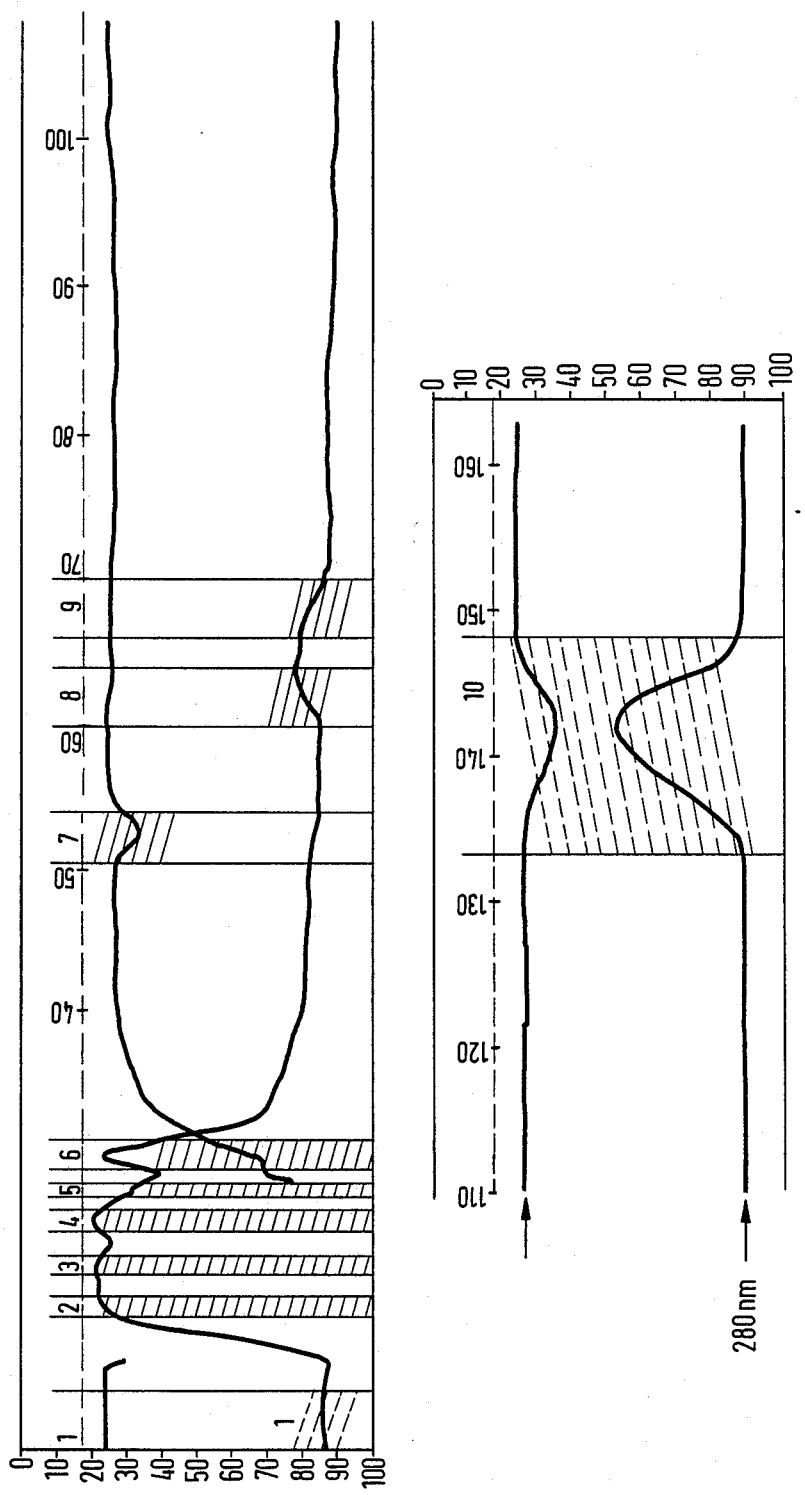

FIG. 2 shows the gel chromatograpic separation.

II. Evaluation of the results of the assays

1. Analysis of amino acids:

Preliminary remark: when summarizing the quantitative data of the amino acid-analysis before and after the acidic total hydrolysis of the substances to be examined minimal peaks and such peaks, which could not be assigned by the analysator in the automatic evaluation are not to be considered.

It is noticeable, that free amino acids can only be indicated as minimal by-products, as it is to be expected for a peptide preparation. The identification of the free amino acids is not without any doubt, because in the separation runs the individual peaks can only be detected as pile extensions of the separation-pattern of the peptides. But attention is drawn to the fact, that, especially at higher sample concentrations (1 mg/500 μl) a reproducible peakpattern is obtained, which does not only permit the identification of the preparation 101/83 as such, but permits also its easy standardization: for example by the peaks at 23.73 (asparaginic acid) and 83.81 (histidine), and by the characteristic peaks at 9.56, 57.15 and 71.15, which are characteristic for peptide separations.

2.1 Polyacrylamide electrophoresis:

Due to the characteristics in the gel electrophoresis it can be deduced, that 101/83 comprises only low molecular peptides with an estimated chain length of not more than 15 amino acids/sequence. Only one extraction product from thymus-tissue without enzymatic partial hydrolysis can be separated with this electrophoresis-technique to a small extent.

But of importance is the simple result, that also with this technique it can be recognized, that 101/83 is richer in peptides than the yellow fraction from thymus (example 2).

2.2 Paper electrophoresis:

A comparison of the separation-pattern of the yellow fraction from thymus with the peptide fraction 101/83 shows significantly, that in the latter case a complex peptide-mixture is present, which because of its polyfunctional, ionic nature is not representable without a chromatographic pre-separation in the electric high voltage field.

3. Determination of end groups:

With the method used all nitrogen-functions are detected, which are not protonated at pH 10.5; therefore not only peptide- and protein-end groups are marked by this method, but also optionally free amino acids, which are present.

Because glycine and alanine as free amino acids are not contained in the preparation, it becomes clear, that these both are the principal peptide end groups in 101/83.

The high content of asparaginic acid and cysteine sulfonic acid, as well as arginine and histidine in the analysis of free amino acids is also proved in the end group-determination, and therefore these amino acids cannot originate from an N-terminal peptide bond.

Glutamic acid, proline and serine are noticably present in the end group-determination, and therefore these amino acids can also be regarded as peptide end groups, because according to the amino acid-analysis only very small amounts are present in the preparation 101/83 in free form.

4. Gel chromatographic characteristics:

In the separation on Sephadex LH 20 the peptide fraction from thymus 101/83 shows a remarkably different behavior as the yellow fraction 69/83 (cf. example 2). The UV-absorption at 280 nm of the main fractions 2 to 6 can be only due to the content of oligonucletides, because the preparation 101/83 contains according to its amino acid composition only 6 weight percent of amino acids (Tyr, Phe, His), which are UV-absorbing.

This is also proved by the electrophoretic results on cellulose-thin layer and by a qualitative examination by HPLC. It is important, that by column-chromatographic separation on Sephadex LH 20 in water the oligonucleotide content of the preparation can be separated from a peptide part (fraction 6). From the elution diagram (FIG. 2) it can also be deduced, that the portions of the preparation 101/83, which are collected together in the fractions 7 to 10, and which are far removed separated from the main components, can only contain substances with a molecular volume of free amino acids and mononucleosides. This is further proved by an additional electrophoretic as well as a thin layer chromatographic examination.

The gel chromatographic fraction 6 from 101/83 has to be regarded as the peptide guiding-fraction of the preparation.

For the pharmaceutical composition according to the present invention it can be expedient, to use as the peptide fraction only the main fractions obtained in the gel chromatography (example 1b, I, 4) or the peptide guiding fraction (fraction 6).

EXAMPLE 2

(a) Procedure for isolating the yellow fraction:

The filtrate of the peptide fraction obtained according to example 1(a) is evaporated under vacuum (inclined tube-rapid rotary evaporator) to about 50% of its volume (the filtrates of the wash alcohol to about 20% of the volume), whereby the temperature should not exceed 60° C.

The concentrate mixture obtained in this manner is applied on aluminum oxide-columns (aluminum oxide Woelm A Super I, type W 200 of Woelm, Eschwege; the filling of the columns is carried out in such a way, that the column is first filled with ethanol, and then the aluminum oxide is added; after 12 hours the column is ready for use). After the application of the concentrate mixture on the chromatographic column washing is carried out with ethanol; the elution is carried out with distilled water under pressure (bacterial filtered compressed air). After the end of the elution the eluate is evaporated under vacuum to about 20% of its volume (inclined tube-evaporator), and from the concentrate such obtained a crystallized dry product (yellow fraction) is obtained by evaporation in the rotary evaporator.

(b) Physical-chemical characterization of the fraction obtained according to example 2(a) (hereinafter designated as 69/83):

I: Equipment for the assays and results 1.1 Preparative separation of the flavines by exclusion-chromatography.

5.007 g and 16 g of the yellow fraction (yellow substance) are separated with a preparative Sephadex ® LH 20-column with the gel bed dimension 3,5×240 cm in water (1% trifluoro ethanol) as the eluents by exclusion chromatography due to the molecular sieve-effect. For this portions of 2×5 g and 1×6 g, respectively, are completely dissolved in 5 ml of distilled water (1% trifluoroethanol) and are applied on the gel bed. Fractions of 19 ml/tube/25 min. are collected and the gel chromatographic separation process is continually monitored 1) by measuring the UV-absorption at 280 nm (flow-photometer Uvicord II of LKB Company) and by 2) flow-refractometry (Waters-refractometer, R 4; damping 64) by measuring the variation in density of the chromatographic eluate.

Figure 3:
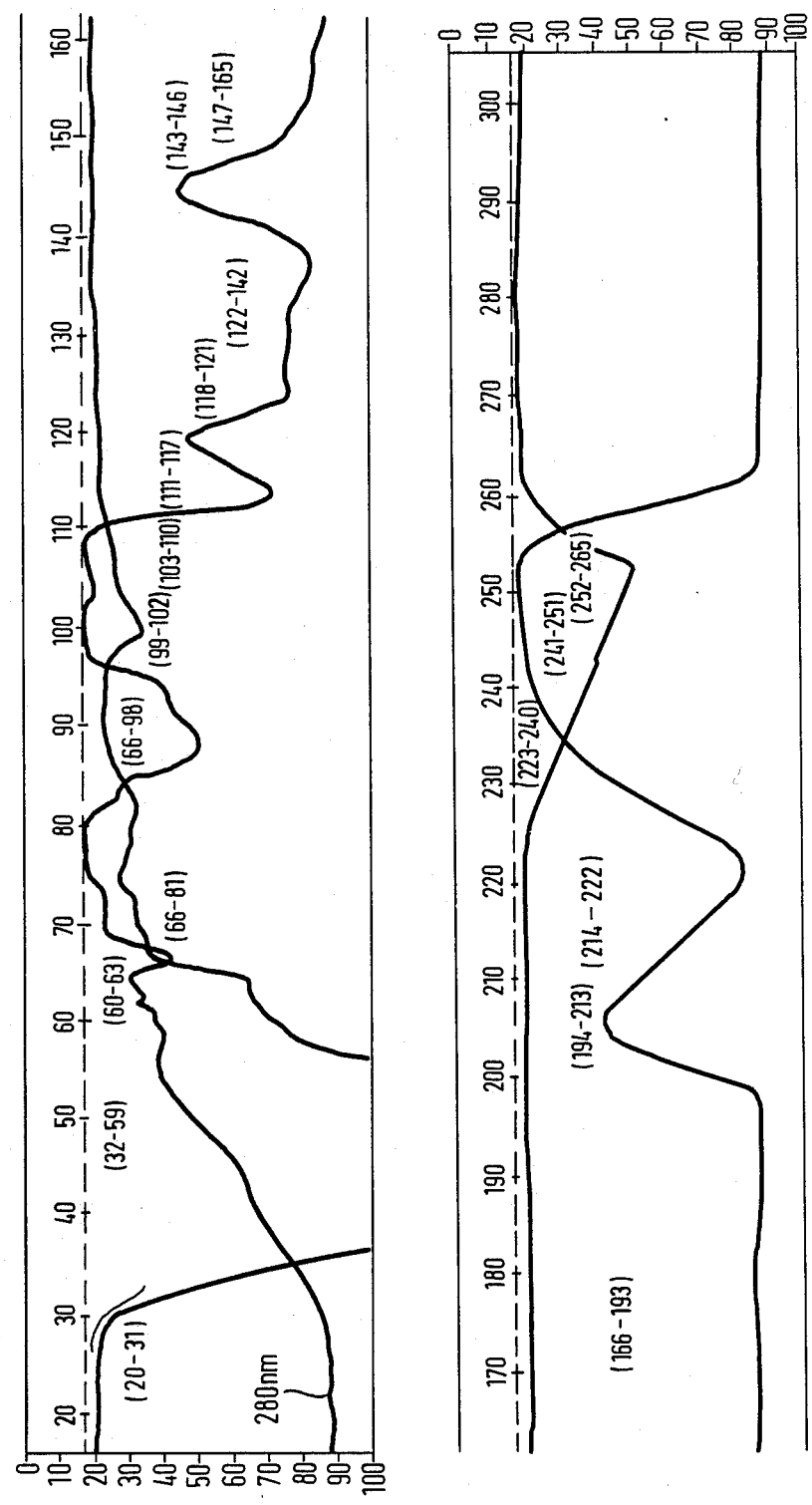

A representative, preparative separation run is shown in FIG. 3 (elution diagram). In the separation runs a heavily yellow colored component migrates as a sharply terminated zone through the separation column and is collected in the range of the tube Nos. 80 to 100, then lyophilized and weighted.

Result:

From 16 g 69/83 a total of 224 mg (1.4 weight percent) of a yellow component is obtained, which hereinafter is analytically and by methods of the chemistry of natural substances examined.

|  | Elementary analysis: | | |
| --- | --- | --- | --- |
|  | C % | H % | N % |
| yellow component | 52.41 | 6.27 | 14.87 |
| Riboflavin | 52.59 | 5.79 | 15.34 |

1.2 Procedure for isolating lyophilized fractions of the gel chromatographic separation of 69/83.

With respect to the concentration and UV-absorption of the separated components after the preparative separation of 5.007 g 69/83 18 fractions are collected together.

For this the contents of the corresponding tubes are poured into round bottomed flasks, which have been weighted before, the tubes were rinsed three times with distilled water, and the fractions corresponding to the combined tubes are marked.

The aqueous fractions are freezed by rotation under vacuum at −78° C., and subsequently lyophilized (lyophilizer Haereus-Leybold, G 2).

The lyophilized fractions are weighed in the corresponding round bottom flasks, air- and moisture-sealed (parafilm) and are stored in a refrigerator at +4° C. for further assays.

Results: from 5.007 g 69/83 the following fractions are obtained.

| Fraction | Weight (mg) |
| --- | --- |
| (20–31) | 38 |
| (32–59) | 3883 |
| (60–65) | 316 |
| (66–81) | 237 |
| (82–98)* | 94* |
| (99–102) | 39 |
| (103–110) | 50 |
| (111–117) | 16 |
| (118–121) | 10 |
| (122–142) | 303 |
| (143–146) | 4 |
| (147–165) | 14 |
| (166–198) | 114 |
| (199–208) | 14 |
| (209–222) | 15 |
| (223–240) | 7 |
| (241–251) | 21 |
| (252–265) | 2 |

*yellow component

The total amount of the lyophilized fractions amounts 5.002 g (99.9%).

1.3a Elementary analysis of dominating fractions of 69/83

| Fraction | Weight-% | C % | H % | N % | S % |
| --- | --- | --- | --- | --- | --- |
| 20–31 | 0.8 | 34.90 | 5.16 | 39.84 | 0.0 |
| 32–59 | 77.6 | 47.81 | 7.43 | 15.73 | 0.95 |
| 60–65 | 6.3 | 53.16 | 7.38 | 12.17 | 0.70 |
| 66–81 | 4.7 | 52.42 | 7.30 | 15.70 | 0.51 |
| 82–98** | 1.9 | 52.41 | 6.27 | 14.87 | 0.0 |
| 99–102 | 0.8 | 46.95 | 4.68 | 26.58 | 0.0 |
| 103–110 | 1.0 | 50.80 | 5.06 | 16.96 | 0.0 |
| 111–117 | 0.4 |  |  |  |  |
| 118–121 | 0.2 | 45.53 | 4.01 | 19.33 | 0.0 |
| 122–142 | 6.1 |  |  |  |  |
| 143–146 | 0.1 | 42.89 | 5.09 | 16.55 | 0.0 |
| 147–165 | 0.3 |  |  |  |  |
| 166–198 | 2.3 |  |  |  |  |
| 199–208 | 0.3 | 36.19 | 7.00 | 26.66 | 0.0 |
| 209–222 | 0.3 |  |  |  |  |
| 223–240 | 0.1 | 28.22 | 3.98 | 10.20 | — |
| 241–251 | 0.4 | 25.85 | 3.14 | 7.64 | — |
| 252–265 | <0.1 | — | — | — | — |

*relating to the total amount of lyophilized fractions (5.002 g)
**yellow component 1.3b Amino acid-analysis of dominating fractions of 69/83

Content of free amino acids:

For the determination of the content of free amino acids an amount of 40 μg to 2 mg are weighed, incorporated into the starting buffer (pH 1.8) without any pretreatment, and examined by means of an automatic amino acid analyzer, in order to determine, which end group markings (cf. 1.3 c) are due to the content of free amino acids, carried along and associated with peptides, in the fractions, and which proportion of the fractions is of peptidic nature.

Results:

1.411 mg of the fraction (20 to 31) contain as free amino acids (nMol) 52.7 cysteine sulfonic acid, 15.4 asparaginic acid, 5.9 threonine, 7.7 serine, 5.1 glycine, 1.8 lysine and 11.3 $NH_4^+$. From the obtained data it follows, that about 1 weight percent of the fraction are free amino acids.

195 μg of the fraction (32 to 59) contain as free amino acids (nMol) 52.1 cysteine sulfonic acid, 6.6 asparaginic acid, 20.7 isoleucine, 25.1 leucine and 49.9 phenyl alanine. From the determination it follows, that about 8 weight percent of the fraction are free amino acids.

204 mg of the fraction (60 to 65) contain as free amino acids (nMol) 2.5 leucine, 108.2 phenylalanine, 54.4 histidine and 27.3 arginine. According to the determination of end groups (cf. 1.3 c) the peak at a retention time of 73.6 could not be assigned to lysine; also the content of histidine and arginine is questionable, because the form of the peaks is not characteristic for these amino acids. With this reservations it follows, that about 16 weight percent of the fraction is free amino acids.

200 μg of the fraction (66–81) contain as free amino acids (nMol) 4.0 tyrosine, 91.9 phenyl alanine, 17 $NH_4^+$, 4,2 histidine and 3.1 arginine. From this it results, that about 1.9 weight percent of the fraction are free amino acids.

40 μg of the fraction (82–98) contain as free amino acids (nMol) 4.9 cysteine sulfonic acid and 1.5 histidine. From this it follows, that about 2.8 weight percent of the fraction are free amino acids.

1.995 mg of the fraction (99–102) contain as free amino acids (nMol) 8.6 leucine, 1.7 tyrosine and 10.4 histidine. From this it follows, that about 0.2 weight percent of the fraction are free amino acids.

2.319 mg of the fraction (103–110) contain as free amino acids (nMol) 1.3 cysteine sulfonic acid, 1.9 cysteine, 4.5 leucine, 2.1 phenyl alanine and 5.9 histidine. From this it follows, that less than 0.1 weight percent of the fraction are free amino acids.

Total content of amino acids, determination of the peptidic portion of the gel-chromatographic obtained fractions:

Initial weight, in each case about 40 μg, of the main fractions (20–31)–(103–110) are totally hydrolyzed in sealed ampoules in 6 N HCl for 24 hours at 120° C., are then evaporated to dryness under vacuum, are incorporated in the starting buffer (pH 1.8) and are examined by means of an automatic analysator for the content of amino acids. From the determined total contents of amino acids the peptide content is scheduled by subtraction of the contents of the fractions of free amino acids.

The results are shown in the following table I:

TABLE I

Total amino acid- and peptide content of the main fractions of 69/83

| | initial weight [μg] | | | | | | |
|---|---|---|---|---|---|---|---|
| | 40 | 40 | 40 | 40 | 50 | 40 | 40 |
| | Fractions | | | | | | |
| Amino-acids | (20–31) | (32–59) | (60–65) | (66–81) | (82–98)* | (99–102) | (103–110) |
| | Content [μg] | | | | | | |
| Csa | 0.161 | 0.204 | 0.481 | 0.369 | 0.237 | 0.390 | 0.337 |
| Asp | 0.738 | 0.764 | 0.463 | 0.435 | 0.211 | 0.083 | 0.271 |
| Thr | 0.281 | 0.557 | 0.308 | 0.293 | 0.197 | 0.102 | 0.097 |
| Ser | 0.305 | 0.423 | 0.314 | 0.287 | 0.200 | 0.087 | 0.067 |
| Glu | 0.436 | 1.069 | 0.511 | 0.526 | 0.520 | 0.385 | 0.235 |
| Pro | 1.151 | 3.259 | 2.665 | 1.820 | 2.511 | 0.738 | 0.773 |
| Gly | 1.698 | 2.869 | 1.013 | 1.950 | 0.730 | 5.489 | 1.772 |
| Ala | 0.831 | 1.714 | 0.557 | 0.963 | 0.497 | — | 0.336 |
| Cys | — | — | — | — | — | — | — |
| Val | 0.379 | 1.125 | 0.851 | 0.777 | 0.425 | 0.065 | 0.107 |
| Met | — | 0.321 | — | — | 0.396 | 0.184 | — |
| Ile | 0.247 | 1.177 | 0.914 | 0.599 | 0.658 | 0.229 | 0.264 |
| Leu | 0.234 | 1.842 | 1.623 | 1.005 | 1.683 | 0.303 | 0.289 |
| Tyr | 0.128 | 0.167 | 1.268 | 1.905 | 0.306 | 0.351 | 0.825 |
| Phe | 0.053 | 0.824 | 9.940 | 5.765 | 0.601 | 0.445 | 2.935 |
| Lys | 0.218 | 0.938 | 1.074 | 0.213 | 0.141 | 0.095 | 0.133 |
| $NH_4^+$ | 1.307 | 0.152 | 0.121 | 0.547 | 0.443 | 1.473 | 1.026 |
| His | — | 0.439 | 0.635 | 0.123 | — | — | — |
| Arg | — | 1.113 | 0.738 | 0.281 | 0.137 | 0.413 | 0.331 |
| Sum [μg] | 8.167 | 18.957 | 23.476 | 17.850 | 9.893 | 10.932 | 9.798 |
| Total-weight-% | 20 | 47 | 59 | 45 | 20 | 27.3 | 25 |
| weight-% of free amino acids | −1 | −8 | −16 | −2 | −3 | −0.2 | −0.0 |
| peptide content, % | 19 | 39 | 43 | 43 | 17* | 27 | 25 |

*yellow component

Qualitative amino acid-analysis of the subfractions (118–121)–(252–265). According to the above stated method samples of about 40 μg, respectively, are examined qualitatively for the content of amino acids after total hydrolysis, in order to have a relation to the end group determinations (cf. 1.3 c).

Results: The latter fractions of the gel chromatographic separation of 69/83, which are with respect to the quantitative proportion unimportant, contain only about 10 to 20 weight percent of peptides and amino acids, with decreasing tendency towards the latter fractions. According to the corresponding elementary analysis (cf. 1.3 a) a content of nucleotide-fragments cannot be excluded.

1.3 c End group determination of the main fractions

The method of end group marking by means of dansyl chloride is used, which in the carried out micro technique permits to detect the N-terminals of amino acids, peptides and proteins in the pico-mol range ($10^{-12}$ M) in 2-dimensional, chromatographic separation.

Dansylation: about 5 μg of the substance to be examined are reacted with dansyl chloride in 0.05 molar $NaHCO_3$-buffer, and are then totally hydrolyzed in a sealed capillary tube in 6 N HCl for 4 hours at 120° C. The hydrolysates are dried under vacuum, incorporated in water and are examined by 2-dimensional chromatography on micro-polyamide plates:

1. dimension, 48% formic acid;
2. dimension, glacial acetic acid/toluene (1:4; v/v).

The N-terminal marked amino acids are identified due to their fluorescence in UV on polyamide plates, and photographed. The assignment is carried out corresponding to the plotting scheme of the dansylated amino acids (cf. example 1 b, I, 3).

Result:

Fraction (20–31), main marking: His;
Background marking (traces): Ser, Asp, Gly.
Fraction (32–59), main marking: Gly, His, His*, Arg, Leu;
Background marking: Asp, Ser, Ala, Val, Pro, Ile, Phe, Tyr, Lys.
Fraction (60–65), main marking: Phe, Asp, Tyr, Ile, Leu, $NH_4^+$, Gly, His, Arg (a diffuse spot at the edge of the left, lower quadrant cannot be assigned);
Background marking: $CySO_3H$, Ala, Val, Lys (traces).
Fraction (66–81), main marking: Phe, Tyr, $NH_4^+$, Gly, Asp; Background marking: His, Ser, Thr, Ala, Val, Ile, Leu
Fraction (82–98), main marking: Tyr;
Background marking: Phe, Ile, Leu, Val, Ala, $NH_4^+$, Gly.
Fraction (99–102), main marking: His, His*, Tyr;
Background marking: Glu, Leu, Phe.
Fraction (103–110), main marking: Gly;
Background marking: Asp.

2. Analytical and preparative HPLC of the yellow component obtained according to 1.1, for the isolation of a flavine-component in pure form For the following stated HPLC-essays a total of 224 mg of the yellow component from 69/83 have been available, which in aqueous solution shows strong fluorescence.

Because according to the elementary analysis of this accumulated flavine-component the idea of riboflavine has been strenghtened (cf. 1), commercially available "riboflavine for biochemical purposes" (Merck) has been used for HPLC-analytical comparison.

Separation column:

Analytical $C_{18}$-reversed-phase-silica gel-columns ($4\times250$ mm; grain size: $5\mu$):

Elution system:

25% methanol in water, 10 minutes; for further 25 minutes an increasing gradient to 50% methanol, followed by a washing step of 12.5 minutes with pure methanol. Afterwards the column is equilibrated according to the starting conditions.

Figure 4:
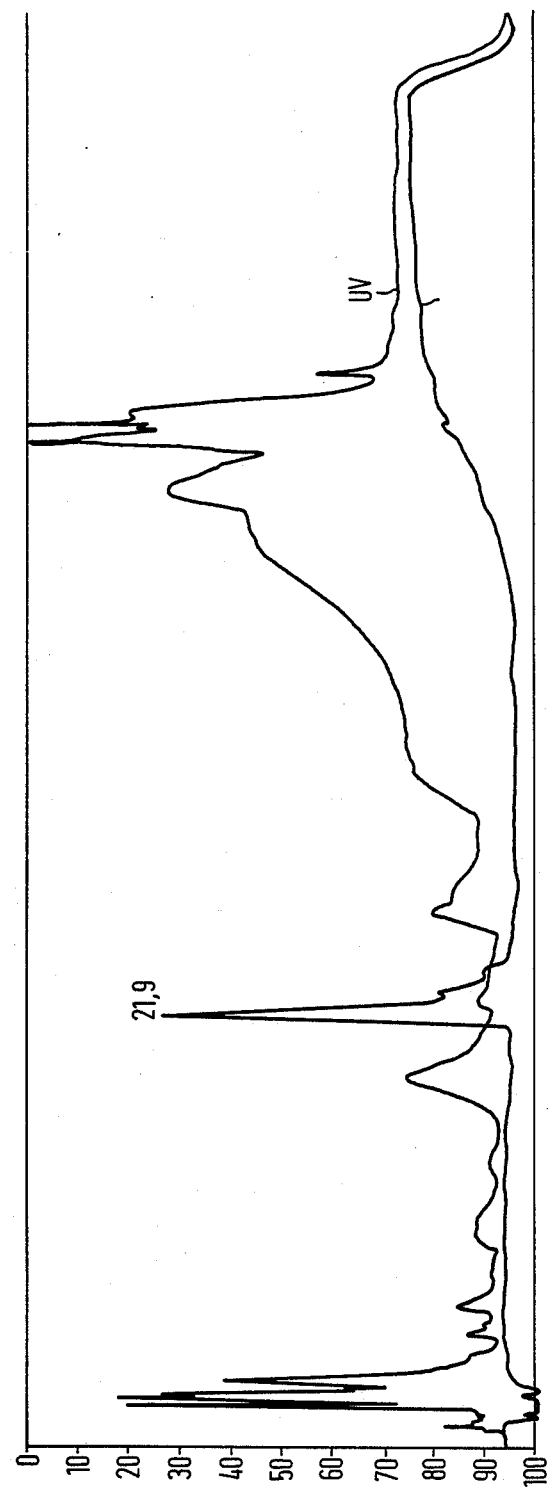

Analytical HPLC:

46.25 $\mu$g/5 $\mu$l methanol:water 1:1 of the yellow component, accumulated according to 1 (c=9.25 $\mu$g/$\mu$l) are injected into a separation column and are eluated at a flowing rate of 1 ml/min. with the above stated gradient system. The paper advance of the recorder is 1 cm/min. The detection is made in the UV-range (210 nm) and in the fluorescence range (excit. 265 nm, amiss. 530 nm). The result is shown in FIG. 4.

Figure 5:
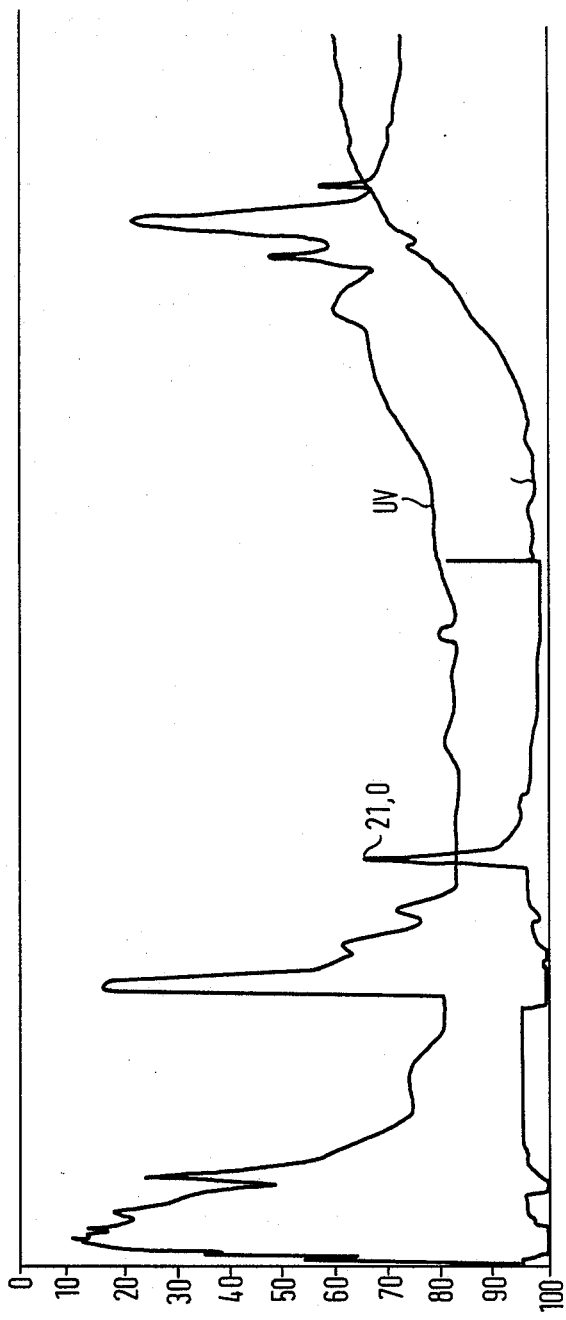

In a further, technically identical run 1.205 mg 69/83 (original substance) dissolved in 5 $\mu$l methanol:water 1:1 are injected into the same analytical HPLC-column. The result is shown in FIG. 5.

In a further, technically identical experiment 3 $\mu$l riboflavine (Merck), dissolved in water (c=714 $\mu$g/ml) are applied on the same analytical separation column.

Result of the analytical comparison:

The yellow component, accumulated on Sephadex LH 20, as well as the original substance 69/83 contain a fluorescent substance, which leaves the analytical HPLC-column exactly at the same retention time of 21 minutes as pure riboflavine (Merck).

The calculation of the concentration by means of the fluorescence curve with reference to the curve of pure riboflavine results in a content of about 0.6% of riboflavine for the component accumulated on Sephadex LH 20.

Figure 6:
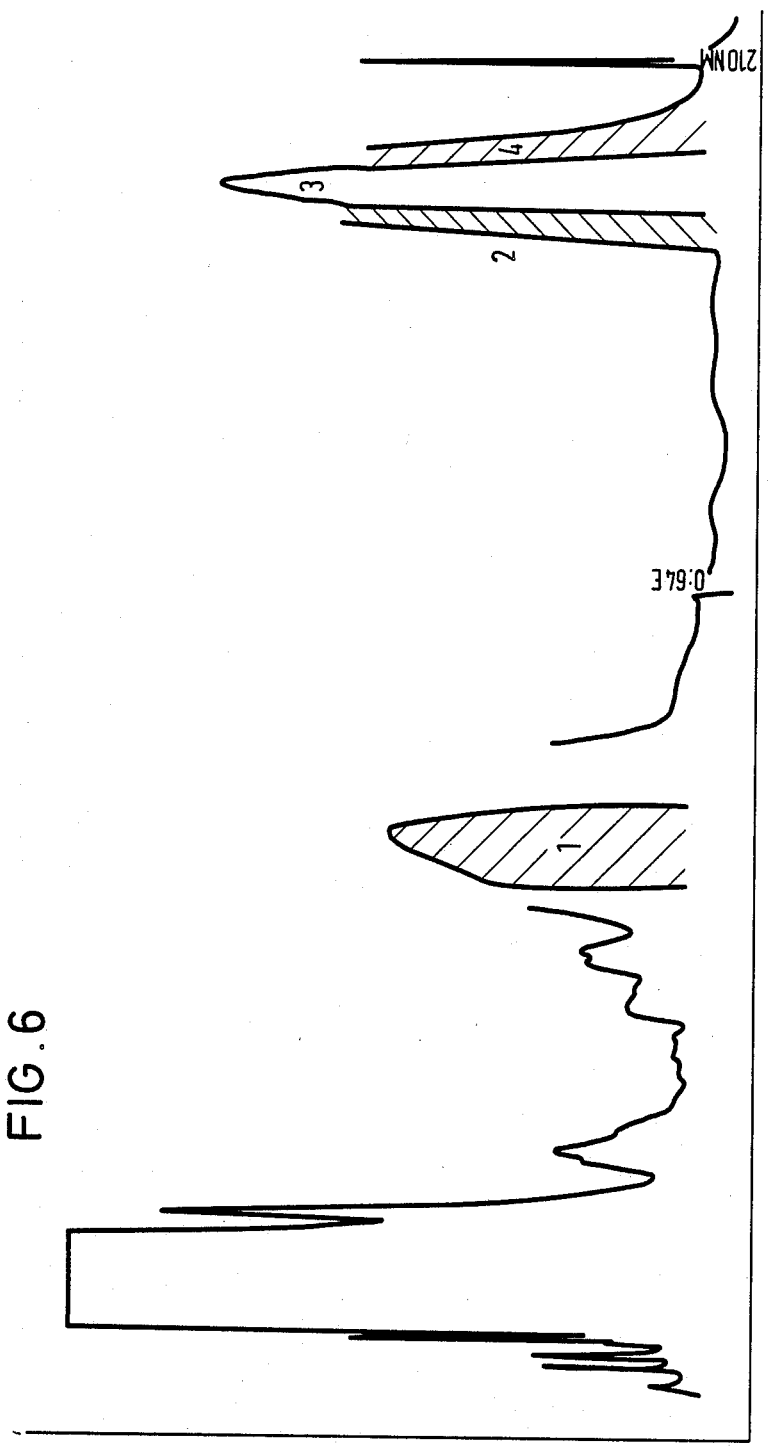

Preparative HPLC:

On a preparative column of the dimension $28\times250$ mm $C_{18}$-reversed-phase-silica gel, grain size: $5\mu$, 129.7 mg of the yellow component, accumulated according to 1, dissolved in 4.2 ml water (5 drops 5 N $NH_4OH$) are separated by an isocratic mixture of methanol/water 18:82. The flow rate is 26 ml/min. at 130 bar; UV-detection at 254 nm, paper advance of the recorder 30 cm/h. The result of the separation is shown in FIG. 6. 2 peaks have been collected in four fractions: fraction 1 contains the first, colorless peak, and the second in the fraction 2, 3 and 4 shows yellow fluorescence. These collected fractions give after lyophilization 3.3 mg of purified flavine-component.

Examination of purity: The three fractions of the flavine-component obtained by preparative HPLC are examined by means of analytical HPLC at the above stated column, using the following, temporarily extended gradient: 10 minutes 25% methanol in water, afterwards during 35 minutes increasing to 60% methanol in water, and afterwards 10 minutes washing with 100% methanol. All other parameters are identical with the above stated.

Result:

All three separation runs show a ratio of the peak areas under the UV- and fluorescence-curve, which is identical with this of pure riboflavine. In the descending shoulder of the fluorescence-graph two small fluorescence-peaks can be seen, which are also detected in pure riboflavin (Merck).

A quantitative amino acid-analysis has been carried out with the colorless fraction 1 of the preparative HPLC-separation after total hydrolysis.

Figure 7:
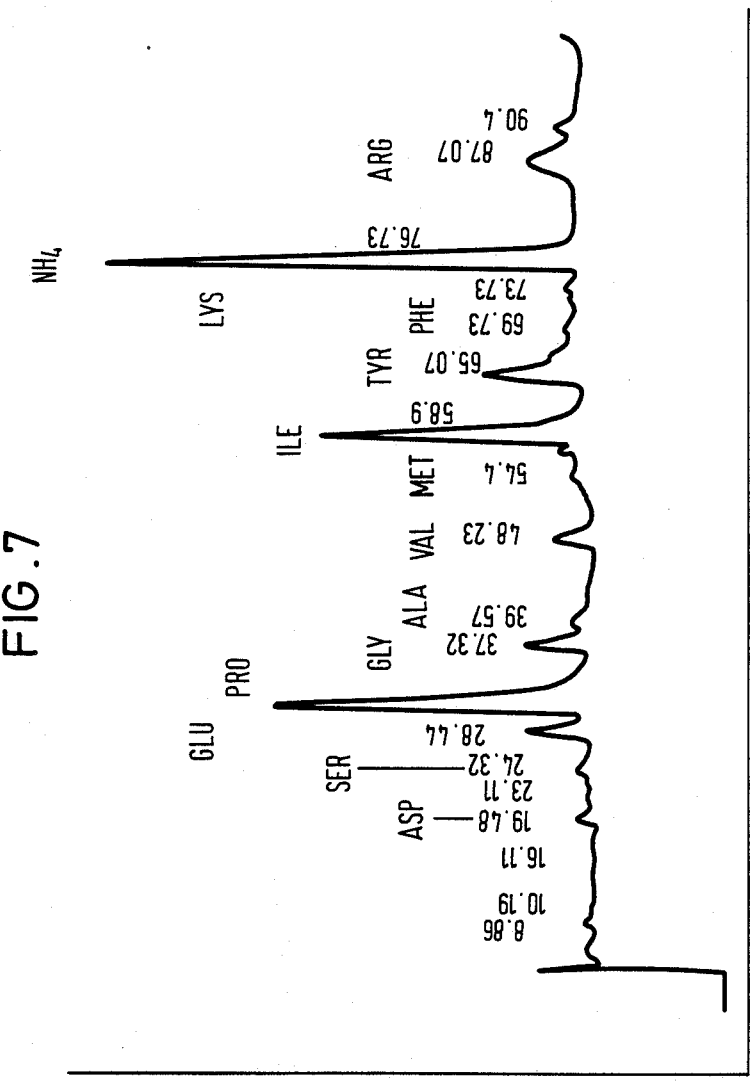

55 $\mu$g of a peptide, associated with the flavine-component, contains the following amino acids (nMol): 2.8 glutaminic acid, 48.9 proline, 3.1 glycine, 1.6 alanine, 2.1 valine, 4.4 isoleucine, 8.0 tyrosine, 1.2 phenyl alanine, 1.5 lysine, 14.9 $NH_4^+$ and 3.8 arginine. The result is shown in FIG. 7.

3. Analytical assays (according to the analysis of natural substances) of the flavine-component isolated from 69/83

Fraction 3 of the preparative HPLC-purification of the flavine-component isolated from 69/83 is used for the structural evidence (according to the analysis of natural substances).

Nuclear resonance spectrum: A 360 MHz $^1H$-NMR-spectrum of the fraction 3 from the preparative HPLC-separation of the flavine-component from 69/83 in $D_2O$ has been recorded.

Result:

The nuclear resonance spectrum shows all structural elements which are characteristic for riboflavine: the signals of the methyl protons on the isoalloxazine-ring at 2.46 ppm and at 2.58 ppm, for the ribit-part at 3.75 ppm, at 3.85 to 4.05 ppm and at 4.35–4.46 ppm, as well as for the aromatic protons at 7.83 to 7.92 ppm.

14 not exchangeable protons are to be expected for riboflavine in $D_2O$. 14 not exchangeable protons have been found.

Mass spectrometric identification:

Fraction 3 of the preparative HPLC-purification of the flavine-component, which has been accumulated from 69/83 by means of exclusion chromatography on Sephadex LH-20, shows the following result in comparison with riboflavine (Merck):

Pure riboflavine (solvent water) results in a distinct field-desorption-mass spectrum with the molecular ion at m/z 376 as the highest signal and with a $(M+Na)^+$-ion at m/z 399. The corresponding field-desorption-mass spectrum of the flavine-component from 69/83 also shows a strong signal for the $(M+H)^+$-ion 377 and a even stronger signal for the ion $(M+Na)^+$ at 399 (solvent water). In comparison with the authentical riboflavine (Merck) the riboflavine isolated by preparative HPLC therefore contains increased amounts of alkali salts. The FAB-mass spectrum (fast atom bombardment) of the direct comparison of riboflavine (Merck) with the riboflavine isolated from 69/83 by means of preparative HPLC shows the identity of both compounds, but in the riboflavine obtained from thymus an additional signal at m/z 367, and its glycine-addition peak at m/z 459. From this it follows, that the riboflavine isolated from 69/83 by means of preparative HPLC contains an accessory amount with the molecular weight of 366. At a higher heating capacity of 24 to 26 mA the molecular peak of the unknown substance at 367 can also be detected in the field-desorption-mass spectrum.

II. Evaluation of the results of the assays

From I, 1.3 b it results, that the separable flavine component contains 17 weight percent of peptide. From this the question arises, whether the peptide content of this component is chemically bound on it or appears, due to lipophilic interaction, associated with the fluorescent body. As it has been proved by means of analytical HPLC on an reverse phase-silica gel ($C_{18}$; $5\mu$) without any doubt, the fluorescent substance eluates with a retention time of 21 minutes, which is identical with authentic riboflavine (Merck); this behavior is not dependent from the fact, whether the fluorescent substance in the original preparation 69/83 has been detected directly by means of analytical HPLC, or from the flavine-component accumulated on Sephadex LH-20. From this it can be deduced, that an accessory amount of peptide cannot be chemically bound on the flavine component, because it would then appear in the HPLC-system different to authentic riboflavin. But nevertheless it is remarkable, that the peptide associated with the flavine-component has to be present in a very stable association, because in the analytical HPLC UV-absorbing components are eluated in immediate vicinity to the fluorescence-peak, and before and after it (for this confer FIG. 4 of the assays).

The peptide portion of the flavine-component, as present after the Sephadex LH-20-accumulation, could be separated from the flavine by means of preparative HPLC in a base line-separation with remarkable efficiency. An amino acid analysis of the separated peptide shows, due to the content of proline, isoleucine, tyrosine and phenyl alanine, significantly the high lipophilic character, and herewith illustrates the close interaction with the flavine.

EXAMPLE 3

Preparation of a pharmaceutical composition (solution for injection)

| Composition per 1 ml: | |
| --- | --- |
| Organ extract fractions (mixture of the two fractions obtainable according to examples 1 and 2) | 10.00 mg |
| phenol (DAB 7) | 4,55 mg |
| NaCl | 5,00 mg |
| water for injection ad | 1,00 ml |
| Amount of batch: 2.2 1 (sufficient for 1000 ampoules ad ml). | |

The ingredients are dissolved in 1.5 1 water, and are then adjusted with 1% NaOH to a pH value of 5.80, and are then supplemented with water to 2.2 1. The obtained solution is sterile filtrated (0.2 $\mu$m membrane filter), and is then filled into 2 ml-ampoules under nitrogen.

EXAMPLE 4

In order to detect the immuno stimulating and immuno regulating properties, respectively, the obtained composition according to the invention (mixture of the peptide fraction obtained according to example 1a and of the yellow fraction obtained according to example 2a) is examined after sterile filtration and lyophilization for its immuno-biological activity on T-lymphocytes and T-cell subpopulations in heparinized human whole blood of healthy donors, without any further additive.

For comparison a sterile filtrated and lyophilized thymus-fraction No. 5 is used.

(a) Collection of the blood samples of healthy donors:

For the blood preparation 11 healthy test persons have been available. By means of a butterfly-shaped syringe 10 ml blood, respectively, are withdrawn from the brachial vein, whereby the volume without suction is passed by means of a silicon tube from the cannula into the heparinized sample tube. This proceeding contributes to the careful treatment of the surface-marker of the T-lymphocytes, which under mechanical stress can lose a portion of the specific receptors.

(b) Culture batches:

10 ml of heparinized whole blood of each donor are divided into four portions of 2.5 ml, respectively, and are supplemented in culture flasks with RPMI 1640-medium to 10 ml (the RPMI-medium has been buffered with isotonic $NaHCO_3$-solution at pH 7.2). The culture flasks are loosely closed and are incubated without any further additive (no fetal calf serum, no heat-denatrated albumin) under sterile conditions in a $CO_2$-incubator at 37° C. for 24 hours.

(c) Preparation of the whole blood-culture batches for cytometry:

Direct marking of the T-lymphocytes and -subpopulations in whole blood with fluorescent, marker specific antibodies (OKT-sera, Ortho Diagnostic Systems). From each of the whole blood-culture batches 100 $\mu$l, respectively, are withdrawn for five markings with OKT-sera, and are incubated with 10 $\mu$l, respectively, of the five Orthomune ® OKT-sera for 30 minutes. Subsequently supplementation with the lyse reagent (ortho diagnostic systems) up to 2 ml/sample is made, then incubation has been carried out for 5 to 10 minutes to destroy the erythrocytes (opaque turbidity) and then measurement is carried out directly in the cytofluorograph (Ortho).

Isolation of T-lymphocytes and -subpopulations for direct marking with fluorescent, marker specific anti bodies (OKT-sera):

The whole blood-culture batches are centrifuged, and the plasma is discarded. The sediment is centrifuged in Ficoll-gradients for 40 minutes at 20° C., and the separated lymphocytes-portion is isolated. Eventually adhering residue-erythrocytes are eliminated by a lyse reagent (ortho diagnostic systems), and the lymphocytes are washed several times by resuspending in PBS and centrifugation.

After repeated resuspension in PBS the lymphocytes are adjusted to $10^7$ cells/ml, and to 100 $\mu$l samples therefrom 10 $\mu$l Orthomune ® OKT-sera, respectively, are added and the such treated samples are stored in an ice bath for 30 minutes, whereby they are agitated after every 10 minutes.

The following fluorescent, monoclonal anti bodies have been used:

OKT-3, specific for peripheral T-lymphocytes;
OKT-4, specific for T-helper-subpopulation;
OKT-6, specific for thymocytes (immature T-cells);
OKT-8, specific for suppressor-(cytotoxic) T-subpopulations;
OKT-11, specific for the E-receptor on peripheral T-cells.

The control - and test cultures of each of the test persons are respectively divided in five measuring-batches according to the marking with the specific OKT-sera.

After the end of the incubation period of 30 minutes for the marking with the monoclonal antibodies OKT-sera in excess are separated by centrifugation and washing for two times with PBS, in order to avoid unspecific fluorescence. The remaining sediment is resuspended in 1 to 2 ml PBS, in a manner that in the total volume about $10^6$ cells remain.

(d) Flow cytometry with the cytofluorograph (ortho diagnostic systems):

By means of the narrow angle-scattered light, which is measured on a unmarked control sample, identical with the sample to be measured, the measuring window of the cytofluorograph is adjusted to the portion of the histogram, which is specific for the lymphocytes, whereby a portion of autofluorescence is eliminated electronically. From each measuring sample 25 to 30 000 cells/30 seconds are evaluated by means of the green fluorescence (specific for the respectively marked T-cell group) and of the narrow angle-scattered light (specific for all lymphocytes). The measuring data are electronically accumulated and are stated as percent of the total lymphocyte number.

(e) Results:

In the following tables 2 to 4 the results are given, which have been obtained by the composition according to the invention, and in the tables 5 to 7 the results are given, which are obtained by the thymosin-fraction No. 5. Table 8 gives a qualitative evaluation in comparison.

The results of the measurements are obtained from the whole blood-cultures at different concentrations, as specified in the tables. The measuring data are assigned to the corresponding control cultures without active ingredients, respectively. The statements in tables 2 and 5 give the %-portion of peripheral human T-cells (OKT-3 positive) as well as of their subpopulations on helper- and suppressor-T-cells (OKT-4 and OKT-8 positive), of immature thymocytes (OKT-6 positive) and of the E-receptor on T-lymphocytes (OKT-11 positive) under the influence of the dosage of the active ingredient as stated).

In all tables it is stated, whether the measuring data are obtained from lymphocytes in whole blood (O) or from lymphocytes which are isolated from the whole blood cultures (i) by direct marking with fluorescent anti-bodies.

The evaluation of the measuring data can be seen from the tables 3 and 6, which are assigned to the tables 2 and 5, respectively.

Calculated are (a) the differences (diff.=%-change) of the T-cell group, respectively, under the influence of the dosage of the active ingredient, in comparison with the same T-cell control group without an addition of active ingredient, and (b) the %-ratio (V) of the measuring data with respect to the control values, whereby the latter amount to 100%.

Statistics of the measuring data are shown in tables 4 and 7. Subdivided corresponding to the kind of T-cell-markings with OKT-ser directly in whole blood (O) or after isolation (i) of the lymphocytes, by means of the number (n) of the individual measurings (M) the standard deviation (S) of the individual measurings from the mean value ($\overline{M}$) are calculated following the formula:

$$S = \sqrt{\frac{M^2 - n\overline{M}^2}{n-1}}$$

Furthermore for each test person a coefficient of variation (CV) has been evaluated, which specifies the biological and methodical range of scatter of the measuring data depending on the blood donation at different days:

$$CV(\%) = \frac{S}{\overline{M}} \cdot 100$$

TABLE 2

(Composition according to the invention)
CYTOFLUOROMETRY
measured values %

| test person | dosage[a] | cells[b] | 3[c] | 4 | 6 | 8 | 11 | 4/8 |
|---|---|---|---|---|---|---|---|---|
| BB$_1$ | K | O | 59.4 | 43.2 | — | 31.4 | — | 1.38 |
| " | 2 | O | 64.6 | 43.4 | — | 34.6 | — | 1.25 |
| " | 4 | O | 68.2 | 41.2 | — | 34.6 | — | 1.19 |
| " | 6 | O | 68.1 | 43.5 | — | 32.9 | — | 1.32 |
| BB$_2$ | K | O | 76.6 | 52.7 | 1.9 | 26.7 | 96.7 | 1.79 |
| " | 2 | O | 76.7 | 51.5 | 1.8 | 27.0 | 97.6 | 1.91 |
| " | 4 | O | 77.8 | 55.0 | 2.0 | 25.3 | 96.2 | 2.17 |
| " | 6 | O | 72.2 | 55.7 | 1.0 | 25.0 | 96.6 | 2.28 |
| GB$_1$ | K | O | 70.7 | 65.4 | — | 10.4 | 79.6 | 6.29 |
| " | 2 | O | 63.8 | 53.0 | — | 15.8 | 79.5 | 3.35 |
| " | 4 | O | 55.8 | 41.7 | — | 16.8 | 88.0 | 2.48 |
| " | 6 | O | 65.7 | 54.3 | — | 17.6 | 85.1 | 3.08 |
| HJG$_1$ | K | O | 71.7 | 28.9 | 0.7 | 39.5 | 75.4 | 0.73 |
| " | 2 | O | 69.9 | 25.0 | 1.4 | 40.5 | 78.6 | 0.63 |
| " | 4 | O | 65.3 | 29.7 | 1.3 | 39.9 | 77.6 | 0.74 |
| " | 6 | O | 69.8 | 29.2 | 1.5 | 41.4 | 77.3 | 0.70 |
| BP$_1$ | K | O | 72.5 | 45.9 | 3.8 | 32.4 | 82.2 | 1.41 |
| " | 2 | O | 68.6 | 45.2 | 0.8 | 31.6 | 80.5 | 1.43 |
| " | 6 | O | 70.7 | 46.0 | 1.1 | 32.3 | 81.6 | 1.42 |
| BB$_3$ | K | O | 66.5 | 42.5 | 6.0 | 24.1 | 86.8 | 1.76 |
| " | 2 | O | 63.0 | 40.6 | 5.8 | 24.9 | 95.0 | 1.63 |
| " | 4 | O | 63.5 | 41.5 | 5.4 | 25.7 | 94.8 | 1.61 |
| " | 6 | O | 63.2 | 43.7 | 6.5 | 23.9 | 92.0 | 1.83 |
| GB$_3$ | K | O | 51.0 | 35.7 | 11.4 | 27.1 | 94.8 | 1.32 |
| " | 2 | O | 59.0 | 43.5 | 11.3 | 18.7 | 93.7 | 2.33 |
| " | 4 | O | 58.4 | 43.0 | 17.7 | 23.2 | 90.1 | 1.85 |
| " | 6 | O | 60.2 | 39.4 | 16.0 | 24.7 | 89.4 | 1.60 |
| UF$_1$ | K | O | 50.5 | 23.2 | 4.1 | 5.71 | — | 4.07 |
| " | 2 | O | 46.0 | 23.8 | 4.3 | 14.4 | — | 1.65 |
| " | 4 | O | 35.6 | 22.7 | 5.5 | 13.3 | — | 1.71 |
| " | 6 | O | 43.4 | 29.8 | 5.8 | 16.4 | — | 1.82 |
| BP$_2$ | K | O | 56.3 | 46.7 | 4.7 | 25.7 | 71.2 | 1.82 |
| " | 2 | O | 70.8 | 43.8 | 2.3 | 21.5 | 69.1 | 2.04 |
| RB$_1$ | K | O | 76.3 | 42.3 | 3.5 | 29.3 | 76.0 | 1.44 |
| " | 2 | O | 71.3 | 46.9 | 1.6 | 38.4 | 67.7 | 1.22 |
| GB$_2$ | K | O | 64.2 | 48.4 | 8.3 | 24.8 | 93.2 | 1.95 |
| " | 2 | O | 66.2 | 47.8 | 10.1 | 23.9 | 97.7 | 2.0 |
| " | 4 | O | 64.1 | 47.3 | 8.7 | 23.2 | 96.8 | 2.04 |
| HJG$_2$ | K | i | 58.5 | 349 | 21.5 | 21.4 | 82.7 | 1.63 |
| " | 2 | i | 62.3 | 39.3 | 11.3 | 30.0 | 72.8 | 1.31 |
| BB$_4$ | K | i | 54.9 | 40.4 | 21.7 | 31.7 | 63.0 | 1.27 |
| " | 2 | i | 53.4 | 45.4 | 27.3 | 37.3 | 67.4 | 1.22 |
| BP$_3$ | K | i | 80.2 | 59.8 | 30.7 | 36.3 | 87.3 | 1.65 |
| " | 2 | i | 73.3 | 60.6 | 39.8 | 48.5 | 75.8 | 1.25 |
| PK$_1$ | K | i | 60.6 | 42.5 | 7.5 | 29.9 | 84.0 | 1.42 |
| " | 2 | i | 58.6 | 42.8 | 5.4 | 27.8 | 76.8 | 1.54 |
| GZ$_1$ | K | i | 73.2 | 55.2 | 17.4 | 23.0 | 79.7 | 2.40 |
| " | 2 | i | 58.5 | 51.2 | 16.4 | 36.3 | 62.4 | 1.41 |
| RL$_1$ | K | i | 70.7 | 54.7 | 17.1 | 34.7 | 69.5 | 1.58 |
| " | 2 | i | 63.1 | 48.9 | 15.0 | 28.5 | 61.1 | 1.72 |
| WL$_1$ | K | i | 83.5 | 39.4 | 11.4 | 31.0 | 87.0 | 1.27 |
| " | 2 | i | 72.9 | 41.8 | 21.4 | 42.0 | 83.6 | 0.99 |
| WL$_2$ | K | i | 70.4 | 34.2 | 12.0 | 31.0 | 82.2 | 1.10 |
| " | 2 | i | 70.2 | 34.2 | 12.8 | 43.3 | 82.2 | 0.79 |
| " | 4 | i | 71.2 | 39.3 | 21.3 | 41.5 | 83.8 | 0.95 |
| BP$_2$ | K | i | 63.2 | 41.4 | 16.3 | 24.3 | 71.2 | 1.70 |
| " | 2 | i | 65.6 | 43.8 | 2.3 | 25.4 | 69.1 | 1.72 |
| UF$_1$ | K | O | 50.5 | 23.2 | 4.0 | 5.71 | — | 4.07 |
| " | 2 | O | 46.0 | 23.8 | 4.3 | 14.4 | — | 1.65 |

TABLE 2-continued (Composition according to the invention)
CYTOFLUOROMETRY
measured values %

| test person | dosage[a] | cells[b] | 3[c] | 4 | 6 | 8 | 11 | 4/8 |
|---|---|---|---|---|---|---|---|---|
| BP$_4$ | K | i | 60.7 | 39.8 | — | 27.5 | — | 1.45 |
| " | 2 | i | 60.9 | 40.0 | — | 25.5 | — | 1.57 |

[a] mg/10 ml whole blood-culture, diluted with RPMI-1640 medium; K = control culture without active ingredient.
[b] Type of direct marking of the T-cells, O in whole blood, i after isolation.
[c] OKT-sera (ortho diagnostic systems), specific for: OKT-3 = total-T-cells; -4 = T-helper-cells, -6 = thymocytes, -8 = T-suppressor cells, -11 = E-receptor on T-cells.

TABLE 3

Evaluation of cytometry

| test person | cells (a) | 3[b] | 4 | 6 | 8 | 11 | 4/8 |
|---|---|---|---|---|---|---|---|
| dosage: 2 mg/10 ml whole blood culture |||||||||
| HJG$_1$ | O | −1.8[c] | −3.9 | +0.7 | +1.0 | +3.2 | −0.10 |
|  |  | 97.5[d] | 86.5 | 200. | 102.5 | 104.2 | 86.3 |
| BP$_1$ | O | 3.9 | 0.7 | −3.0 | −0.6 | −1.7 | +0.02 |
|  |  | 94.6 | 98.5 | 21.0 | 97.5 | 97.9 | 101.4 |
| BB$_1$ | O | +8.3 | +0.2 | — | +3.2 | — | −0.13 |
|  |  | 114.0 | 100.4 |  | 110.2 |  | 90.6 |
| BB$_2$ | O | +0.1 | −1.2 | −0.1 | +0.3 | +0.9 | +0.12 |
|  |  | 100.1 | 97.7 | 94.7 | 101.1 | 100.9 | 106.7 |
| GB$_1$ | O | −6.9 | −12.4 | — | +5.4 | −0.1 | −2.94 |
|  |  | 90.2 | 81.0 |  | 151.9 | 99.9 | 53.3 |
| BP$_2$ | O | +14.5 | −2.9 | −2.4 | −4.2 | −2.1 | +0.22 |
|  |  | 125.7 | 93.8 | 48.9 | 83.7 | 97.0 | 112.1 |
| RB$_1$ | O | −5.0 | +4.6 | −1.9 | +9.1 | −8.3 | −0.22 |
|  |  | 93.4 | 111.0 | 45.7 | 131.1 | 89.1 | 84.7 |
| GB$_2$ | O | +2.0 | −0.6 | +1.8 | −0.9 | +4.5 | +0.05 |
| BB$_3$ | O | −3.5[c] | −1.9 | −0.2 | +0.8 | +8.2 | −0.13 |
|  |  | 94.7[d] | 95.5 | 96.7 | 103.3 | 109.4 | 92.6 |
| GB$_3$ | O | +8.0 | −7.8 | −0.1 | −2.4 | −1.1 | +1.01 |
|  |  | 115.7 | 121.8 | 99.1 | 88.6 | 98.8 | 176.5 |
| HJG$_2$ | i | +3.8 | +4.4 | −10.2 | +8.6 | −9.9 | −0.32 |
|  |  | 106.5 | 112.6 | 52.6 | 140.2 | 88.0 | 80.4 |
| BB$_4$ | i | −1.5 | +5.0 | +5.6 | +5.6 | +4.4 | −0.05 |
|  |  | 97.3 | 112.4 | 125.8 | 117.7 | 107.0 | 96.1 |
| BP$_3$ | i | −6.9 | +0.8 | +9.1 | +12.2 | −11.5 | −0.40 |
|  |  | 91.4 | 101.3 | 129.6 | 133.6 | 86.8 | 75.8 |
| RK$_1$ | i | −2.0 | +0.3 | −2.1 | −2.1 | −7.2 | +0.12 |
|  |  | 96.7 | 100.7 | 72.0 | 93.0 | 91.4 | 108.4 |
| GZ$_1$ | i | −14.7 | −4.0 | −1.0 | +13.3 | −17.3 | −0.99 |
|  |  | 79.9 | 92.7 | 94.2 | 157.8 | 78.3 | 58.7 |
| RL$_1$ | i | −7.6 | −5.8 | −2.1 | −6.2 | −8.4 | +0.1 |
|  |  | 89.2 | 89.4 | 87.7 | 82.1 | 87.9 | 108.9 |
| WL$_1$ | i | −10.6 | +2.4 | +10.0 | +11.0 | −3.4 | 108.9 |

TABLE 3-continued

Evaluation of cytometry

| test person | cells (a) | 3[b] | 4 | 6 | 8 | 11 | 4/8 |
|---|---|---|---|---|---|---|---|
|  |  | 87.3 | 106.1 | 187.7 | 135.5 | 96.1 | 77.9 |
| WL$_2$ | i | −0.2 | ±0 | +0.8 | +12.3 | ±0 | −0.31 |
|  |  | 99.7 | 100.0 | 106.7 | 139.7 | 100.0 | 71.8 |
| BP$_2$ | i | +2.4[c] | +2.4 | +6.7 | +1.1 | −2.1 | +0.02 |
|  |  | 103.8[d] | 105.8 | 114.1 | 104.5 | 97.0 | 101.2 |
| UF$_1$ | i | −4.5 | +0.6 | +0.3 | +8.7 | — | −2.24 |
|  |  | 91.1 | 102.6 | 107.5 | 252.6 |  | 40.5 |
| BP$_4$ | i | +0.2 | +0.2 | — | −2.6 | — | +0.12 |
|  |  | 100.3 | 100.5 |  | 92.7 |  | 108.3 |
| dosage: 4 mg/10 ml whole blood culture |||||||||
| GB$_2$ | O | −0.1 | −1.1 | +0.4 | −1.6 | +3.6 | +0.09 |
|  |  | 99.8 | 97.7 | 104.8 | 93.5 | 103.9 | 104.6 |
| WL$_2$ | i | +0.8 | +5.1 | +9.3 | +10.5 | +1.6 | −0.15 |
|  |  | 101.1 | 114.9 | 177.5 | 133.9 | 101.9 | 86.4 |
| BB$_1$ | O | +8.8 | −2.0 | — | +3.2 | — | −0.19 |
|  |  | 114.8 | 95.4 |  | 110.2 |  | 86.2 |
| BB$_2$ | O | +1.2 | +2.3 | +0.1 | −1.4 | −0.5 | +0.38 |
|  |  | 101.6 | 104.4 | 105.3 | 94.8 | 99.5 | 121.2 |
| GB$_1$ | O | −14.9 | −23.7 | — | +6.4 | +8.4 | −3.81 |
|  |  | 78.9 | 63.8 |  | 161.5 | 110.5 | 39.4 |
| HJG$_1$ | O | −6.4 | +0.8 | +0.6 | +0.4 | +2.2 | +0.01 |
|  |  | 91.1 | 102.8 | 185.7 | 101.0 | 102.9 | 101.4 |
| BB$_3$ | O | −3.0 | −1.0 | −0.6 | +0.8 | +8.0 | 0.15 |
|  |  | 95.5 | 97.6 | 90.0 | 106.6 | 109.2 | 91.5 |
| GB$_3$ | O | +7.4[c] | +7.3 | +6.3 | −3.9 | −4.7 | +0.15 |
|  |  | 104.5[d] | 120.4 | 155.3 | 85.6 | 95.0 | 140.1 |
| UF$_1$ | i | −14.9 | −0.5 | +1.5 | +7.6 | — | −2.36 |
|  |  | 70.5 | 97.8 | 137.5 | 233.3 |  | 42.0 |
| dosage: 6 mg/10 ml whole blood culture |||||||||
| BB$_1$ | O | +8.7 | +0.3 | — | +1.5 | — | −0.06 |
|  |  | 114.6 | 100.7 |  | 104.8 |  | 95.6 |
| BB$_2$ | O | +0.6 | +3.0 | −0.9 | −1.7 | −0.1 | +0.49 |
|  |  | 100.8 | 105.7 | 52.6 | 93.6 | 99.9 | 127.4 |
| GB$_1$ | O | −5.0 | −14.1 | — | +6.9 | +7.4 | −3.33 |
|  |  | 91.9 | 78.4 |  | 166.3 | 109.3 | 47.1 |
| HJG$_1$ | O | −1.9 | +0.3 | +0.8 | +1.9 | +1.9 | −0.03 |
|  |  | 97.3 | 101.0 | 214.3 | 104.8 | 102.5 | 95.9 |
| BP$_1$ | O | −1.8 | +0.1 | −2.7 | −0.1 | −0.6 | +0.01 |
|  |  | 97.5 | 100.2 | 28.9 | 99.7 | 99.3 | 100.7 |
| BB$_3$ | O | −3.3 | +1.2 | +0.5 | −0.2 | +5.2 | +0.07 |
|  |  | 95.0 | 102.8 | 108.3 | 99.2 | 106.0 | 104.0 |
| GB$_3$ | O | +9.2 | +3.7 | +5.6 | −2.4 | −5.4 | +0.28 |
|  |  | 118.0 | 110.3 | 140.3 | 91.1 | 94.3 | 121.2 |
| UF$_1$ | i | −16.1 | +6.6 | +1.8 | +10.7 | — | −2.25 |
|  |  | 68.1 | 128.4 | 145.0 | 287.7 |  | 44.7 |

[a] type of direct marking of the T-cells, O in whole blood, i after isolation.
[b] The figures give the specifity of the OKT-sera (cf. the context).
[c] Diff. (%), change with respect to the corresponding control culture
[d] V(%), %-ratio of the measured value with respect to the corresponding control value, which amounts 100%.

TABLE 4

Statistics of the evaluations

| type of statistics[a] | 3[b] | 4 | 6 | 8 | 11 | 4/8 |
|---|---|---|---|---|---|---|
| Control cultures without active ingredient ||||||||
| n | 21 | 21 | 18 | 21 | 18 | 21 |
| $\bar{M} \pm s$ | 66.2 ± 9.4 | 43.1 ± 9.0 | 11.1 ± 8.2 | 26.8 ± 7.9 | 81.2 ± 9.1 | 1.88 ± 1.20 |
| cv | 14.2 | 21 | 74 | 29.5 | 11.2 | 63.9 |
| n | 10 | 10 | 8 | 10 | 9 | 10 |
| $\bar{M}_o \pm s$ | 66.5 ± 8.6 | 43.9 ± 7.4 | 5.0 ± 3.5 | 26.5 ± 7.7 | 84.0 ± 9.3 | 1.99 ± 1.55 |
| cv | 13.0 | 16.8 | 69.6 | 29.0 | 11.1 | 78.0 |
| n | 11 | 11 | 10 | 11 | 9 | 11 |
| $\bar{M}_i \pm s$ | 66.0 ± 10.4 | 42.3 ± 10.6 | 16.0 ± 7.7 | 26.9 ± 8.5 | 78.5 ± 8.6 | 1.78 ± 0.83 |
| cv | 15.8 | 25.1 | 48 | 31.5 | 10.9 | 46.8 |
| dosage: 2 mg/10 ml whole blood culture ||||||||
| n | 21 | 21 | 18 | 21 | 18 | 21 |
| $\bar{M} \pm s$ | 64.8 ± 7.3 | 43.5 ± 8.4 | 11.7 ± 10.7 | 30.3 ± 9.3 | 78.4 ± 11.6 | 1.57 ± 0.58 |
| cv | 11.2 | 19.2 | 91.2 | 30.6 | 14.8 | 36.9 |
| n | 10 | 10 | 8 | 10 | 9 | 10 |
| $\bar{M}_o \pm s$ | 67.7 ± 5.0 | 44.2 ± 7.5 | 4.4 ± 4.2 | 27.7 ± 8.3 | 84.4 ± 11.9 | 1.78 ± 0.74 |
| cv | 7.4 | 16.9 | 95.3 | 30.1 | 14.1 | 41.7 |
| n | 11 | 11 | 10 | 11 | 9 | 11 |
| $\bar{M}_i \pm s$ | 62.2 ± 8.3 | 42.9 ± 9.4 | 17.7 ± 10.7 | 32.6 ± 9.8 | 72.4 ± 8.0 | 1.38 ± 0.30 |
| cv | 13.3 | 22.0 | 60.4 | 30.2 | 11.1 | 21.9 |

TABLE 4-continued

| | | | | | | |
|---|---|---|---|---|---|---|
| n | 21 | 21 | 18 | 21 | 18 | 21 |
| $\overline{\text{Diff}} \pm s$ | −1.42 ± 6.7 | −0.44 ± 4.1 | 0.81 ± 4.7 | +3.50 ± 6.0 | −2.9 ± 6.5 | −0.27 ± 0.86 |
| cv | 469 | 941 | 580 | 172 | 223 | 318 |
| n | 10 | 10 | 8 | 10 | 9 | 10 |
| $\overline{\text{Diff}_o} \pm s$ | +1.18 ± 7.0 | −0.65 ± 5.25 | −0.65 ± 1.64 | +1.17 ± 3.87 | +0.39 ± 4.67 | −0.21 ± 1.02 |
| cv | 590 | 805 | 252 | 331 | 1198 | 486 |
| n | 11 | 11 | 10 | 11 | 9 | 11 |
| $\overline{\text{Diff}_i} \pm s$ | −3.78 ± 5.68 | +0.57 ± 3.06 | +1.71 ± 6.19 | +5.6 ± 6.9 | −6.15 ± 6.58 | −0.40 ± 0.75 |
| cv | 150 | 537 | 362 | 124 | 107 | 187 |
| n | 21 | 21 | 18 | 21 | 18 | 21 |
| $\overline{V} \pm s$ | 98.7 ± 10.5 | 100.4 ± 9.4 | 100.3 ± 45.4 | 119.8 ± 38.0 | 96.4 ± 8.1 | 92.1 ± 27.6 |
| cv | 10.6 | 9.3 | 45.3 | 31.7 | 8.4 | 30.0 |
| n | 10 | 10 | 8 | 10 | 9 | 10 |
| $\overline{V}_o \pm s$ | 102.9 ± 11.7 | 98.5 ± 11.4 | 91.0 ± 55.6 | 106.6 ± 20.4 | 100.2 ± 5.7 | 100.7 ± 31.3 |
| cv | 11.4 | 11.6 | 61.1 | 19.2 | 5.7 | 31.0 |
| n | 11 | 11 | 10 | 11 | 9 | 11 |
| $\overline{V}_i \pm s$ | 94.8 ± 7.85 | 102.2 ± 7.1 | 107.8 ± 36.7 | 131.8 ± 46.8 | 92.5 ± 8.5 | 84.4 ± 22.5 |
| cv | 8.3 | 7.0 | 34.1 | 35.5 | 9.2 | 26.6 |
| | | Dosage: 4 mg/10 ml whole blood culture | | | | |
| n | 9 | 9 | 7 | 9 | 7 | 9 |
| $\overline{\text{Diff}} \pm s$ | −2.3 ± 8.5 | −1.4 ± 8.9 | +2.5 ± 3.8 | +2.4 ± 4.8 | +2.7 ± 4.6 | −0.63 ± 1.5 |
| cv | 370 | 636 | 152 | 200 | 171 | 232 |
| n | 9 | 9 | 7 | 9 | 7 | 9 |
| $\overline{V} \pm s$ | 95.3 ± 13.5 | 99.4 ± 15.8 | 136.6 ± 37.8 | 124.5 ± 47.1 | 103.3 ± 5.4 | 90.3 ± 33.0 |
| cv | 14.2 | 15.9 | 27.7 | 37.8 | 5.2 | 36.6 |
| | | dosage: 6 mg/10 ml whole blood culture | | | | |
| n | 8 | 8 | 6 | 8 | 6 | 8 |
| $\overline{\text{Diff}} \pm s$ | −1.2 ± 8.0 | −0.8 ± 6.1 | +0.9 ± 2.8 | +2.1 ± 4.5 | 1.4 ± 4.5 | −0.6 ± 1.39 |
| cv | 66.7 | 762 | 311 | 214 | 321 | 232 |
| n | 8 | 8 | 6 | 8 | 6 | 8 |
| $\overline{V} \pm s$ | 97.9 ± 15.2 | 103.4 ± 13.8 | 114.9 ± 67.5 | 130.9 ± 67.8 | 101.9 ± 5.3 | 92.1 ± 30.7 |
| cv | 15.5 | 13.3 | 58.7 | 51.8 | 5.2 | 33.3 |
| | Activity of the preparation on blood samples of different days of the same donor | | | | | |
| test person | control cultures without active ingredient | | | | | |
| n | 5 | 5 | 4 | 5 | 4 | 5 |
| BP $\overline{M} \pm s$ | 66.6 ± 9.6 | 46.7 ± 8.01 | 12.6 ± 12.5 | 29.2 ± 4.99 | 78.0 ± 8.1 | 1.64 ± 0.17 |
| cv | 14.5 | 17.2 | 99.2 | 17.1 | 10.4 | 10.5 |
| n | 4 | 4 | 3 | 4 | 3 | 4 |
| BB $\overline{M} \pm s$ | 64.4 ± 9.4 | 44.7 ± 5.46 | 9.87 ± 10.4 | 28.5 ± 3.71 | 82.2 ± 17.3 | 1.55 ± 0.26 |
| cv | 14.6 | 12.2 | 106 | 13.0 | 21.1 | 17.0 |
| | | dosage: 2 mg/10 ml whole blood culture | | | | |
| n | 5 | 5 | 4 | 5 | 4 | 5 |
| BP $\overline{M} \pm s$ | 67.8 ± 4.8 | 46.7 ± 8.01 | 16.5 ± 16.1 | 30.5 ± 10.7 | 73.6 ± 5.6 | 1.61 ± 0.36 |
| cv | 7.1 | 17.2 | 97.4 | 35.1 | 7.6 | 21.5 |
| n | 5 | 5 | 4 | 5 | 4 | 5 |
| BB $\overline{\text{Diff}} \pm s$ | +1.26 ± 8.23 | −0.04 ± 1.75 | +2.6 ± 6.2 | +1.30 ± 6.39 | −4.5 ± 5.1 | −0.03 ± 0.03 |
| cv | 653 | 4377 | 238 | 491 | 113 | 106 |
| n | 5 | 5 | 4 | 5 | 4 | 5 |
| BP $\overline{V} \pm s$ | 103.2 ± 13.5 | 100.0 ± 4.4 | 78.4 ± 51.8 | 102.4 ± 19.0 | 94.7 ± 5.3 | 97.6 ± 15.4 |
| cv | 13.1 | 4.4 | 66.1 | 18.6 | 5.6 | 15.8 |
| n | 4 | 4 | 3 | 4 | 3 | 4 |
| BB $\overline{M} \pm s$ | 65.2 ± 9.70 | 45.2 ± 4.62 | 11.6 ± 13.7 | 30.9 ± 5.94 | 86.7 ± 16.7 | 1.5 ± 0.33 |
| cv | 14.9 | 10.2 | 118 | 19.2 | 19.3 | 22.0 |
| n | 4 | 4 | 3 | 4 | 3 | 4 |
| BB $\overline{\text{Diff}} \pm s$ | +0.85 ± 5.18 | +0.52 ± 3.11 | +1.77 ± 3.32 | +2.47 ± 2.44 | +4.50 ± 3.65 | −0.47 ± 0.12 |
| cv | 609 | 598 | 188 | 98.8 | 81.1 | 25.1 |
| n | 4 | 4 | 3 | 4 | 3 | 4 |
| BB $\overline{V} \pm s$ | 101.5 ± 8.6 | 101.5 ± 7.54 | 105.7 ± 17.4 | 108.1 ± 7.50 | 105.8 ± 4.38 | 96.5 ± 7.17 |

TABLE 4-continued

| cv | 8.5 | 7.4 | 16.5 | 6.9 | 4.1 | 7.4 |
|---|---|---|---|---|---|---|

[a] abbreviations of the statistics:
n = number of samples,
$\overline{M}$ = measured mean value,
S = standard deviation,
cv = coefficient of variation;
Diff. = mean value of the %-change of the measured culture data with respect to the control culture.
$\overline{V}$ = mean value of the %-ratio of the measured culture data with respect to the control culture data, which amount 100%.
o = marking in whole blood,
i = marking after isolation of the T-cells.
[b] The figures give the specifity of the OKT-sera (cf. context).

TABLE 5

CYTOFLUOROMETRY
Thymosin fraction No. 5
measured values %

| test person | dosage[a] | cells[b] | 3[c] | 4 | 6 | 8 | 11 | 4/8 |
|---|---|---|---|---|---|---|---|---|
| WL$_2$ | K | i | 70.4 | 34.2 | 12.0 | 31.0 | 82.2 | 1.10 |
| " | 2 | i | 76.1 | 44.3 | 25.6 | 55.1 | 86.4 | 0.80 |
| WL$_1$ | K | i | 83.5 | 39.4 | 11.4 | 31.0 | 87.0 | 1.27 |
| " | 2 | i | 84.7 | 39.4 | 14.6 | 40.0 | 85.9 | 0.98 |
| BB$_4$ | K | i | 54.9 | 40.4 | 21.7 | 31.7 | 63.0 | 1.27 |
| " | 2 | i | 55.0 | 49.1 | 26.2 | 39.9 | 62.5 | 1.23 |
| RL$_1$ | K | i | 70.7 | 54.7 | 17.1 | 34.7 | 69.5 | 1.58 |
| " | 2 | i | 67.1 | 53.7 | 16.3 | 31.1 | 67.5 | 1.73 |
| BP$_3$ | K | i | 80.2 | 59.8 | 30.7 | 36.3 | 87.3 | 1.65 |
| " | 2 | i | 75.3 | 63.6 | 28.2 | 34.5 | 85.9 | 1.84 |
| HJG$_2$ | K | i | 58.5 | 34.9 | 21.5 | 21.4 | 82.7 | 1.63 |
| " | 2 | i | 60.4 | 38.8 | 14.6 | 25.7 | 67.6 | 1.51 |
| GZ$_1$ | K | i | 73.2 | 55.2 | 17.4 | 23.0 | 79.7 | 2.40 |
| " | 2 | i | 84.1 | 71.8 | 35.2 | 51.6 | 85.9 | 1.39 |
| GB$_2$ | K | O | 64.2 | 48.4 | 8.3 | 24.8 | 93.2 | 1.95 |
| " | 2 | O | 64.7 | 50.7 | 8.9 | 22.1 | 97.7 | 2.29 |
| " | 4 | O | 68.4 | 52.0 | 3.4 | 24.4 | 97.1 | 2.13 |
| BP$_2$ | K | O | 56.3 | — | — | 25.7 | — | — |
| " | 2 | O | 71.4 | — | — | 21.8 | — | — |
| BP$_2$ | K | i | 63.2 | 41.4 | 16.3 | 24.3 | 71.2 | 1.70 |
| " | 2 | i | 68.7 | 43.7 | 5.3 | 26.1 | 76.0 | 1.67 |
| BP$_4$ | K | i | 60.7 | 39.8 | — | 27.5 | — | 1.45 |
| " | 2 | i | 60.9 | 38.7 | — | 25.2 | — | 1.54 |
| BB$_5$ | K | O | 76.5 | 42.5 | 7.0 | 24.7 | 80.8 | 1.72 |
| " | 2 | O | 72.3 | 43.6 | 4.2 | 47.9 | 90.5 | 0.91 |

[a] mg/10 ml whole blood culture, diluted with RPMI-1640 medium; K = control culture without active ingredient.
[b] Type of direct marking of the T-cells, O in whole blood, i after isolation.
[c] OKT-sera (ortho diagnostic systems), specific for: OKT-3 = total-T-cells; −4 = T-helper-cells, −6 = thymocytes, −8 = T-suppressor cells, −11 = E-receptor on T-cells.

TABLE 6

Evaluation of Cytometry
Thymosin fraction No. 5
dosage: 2 mg/10 ml whole blood culture

| test person | cells[a] | 3[b] | 4 | 6 | 8 | 11 | 4/8 |
|---|---|---|---|---|---|---|---|
| BP$_3$ | i | −4.9[c] | +3.8 | −2.5 | −1.8 | −1.4 | +0.19 |
|  |  | 93.9[d] | 106.4 | 91.9 | 95.0 | 98.4 | 111.5 |
| HJG$_2$ | i | +1.9 | +3.9 | −6.9 | +4.3 | −15.1 | −0.12 |
|  |  | 103.2 | 111.2 | 67.9 | 120.1 | 81.7 | 92.6 |
| GZ$_1$ | i | +10.9 | +16.6 | +17.8 | +28.6 | +6.2 | −1.01 |
|  |  | 114.9 | 130.1 | 202.3 | 224.3 | 107.8 | 57.9 |
| GB$_2$ | O | +0.5 | +2.3 | +0.6 | −2.7 | +4.5 | +0.34 |
|  |  | 100.8 | 104.8 | 107.2 | 89.1 | 104.8 | 117.4 |
| WL$_2$ | i | +5.7 | +10.1 | +13.6 | +24.1 | +4.2 | −0.30 |
|  |  | 108.1 | 129.5 | 213.3 | 177.7 | 105.1 | 72.7 |
| WL$_1$ | i | +1.2 | 0 | +3.2 | +9.0 | −1.1 | −0.29 |
|  |  | 101.4 | 100.0 | 128.1 | 129.0 | 98.7 | 77.2 |
| BB$_4$ | i | +0.1 | +8.7 | +4.5 | +8.2 | −0.5 | −0.04 |
|  |  | 100.2 | 121.5 | 120.7 | 125.9 | 99.2 | 96.9 |
| RL$_1$ | i | −3.6 | −1.0 | −0.8 | −3.6 | −2.0 | +0.15 |
|  |  | 94.9 | 98.2 | 95.3 | 89.6 | 97.1 | 109.5 |
| BP$_2$ | O | +15.1 | — | — | −3.9 | — | — |
|  |  | 126.8 | — | — | 84.8 | — | — |
| BP$_2$ | i | +5.5 | +2.3 | −11.0 | +1.8 | +4.8 | −0.03 |
|  |  | 108.7 | 105.6 | 32.5 | 107.4 | 106.7 | 98.2 |
| BP$_4$ | i | +0.2 | −1.1 | — | −2.3 | — | +0.01 |
|  |  | 100.3 | 97.2 | — | 91.6 | — | 106.2 |
| BB$_5$ | O | −4.2 | +1.1 | −2.8 | +23.2 | +9.7 | −0.01 |
|  |  | 94.5 | 102.6 | 60.0 | 193.9 | 112.0 | 52.9 |

[a] Type of direct marking of the T-cells, O in whole blood, i after isolate
[b] The figures give the specifity of the OKT-sera (cf. the context).
[c] Diff. (%), change with respect to the corresponding control culture.
[d] $\overline{V}$ (%), %-ratio of the measured value with respect to the corresponding control value, which amounts 100%.

TABLE 7

Statistics of the evaluations Thymosin fraction No. 5

| type of statistics[a] | 3[b] | 4 | 6 | 8 | 11 | 4/8 |
|---|---|---|---|---|---|---|
| | control culture without active ingredient | | | | | |
| n | 12 | 11 | 10 | 12 | 10 | 11 |
| $\overline{M} \pm s$ | 67.7 ± 9.5 | 44.6 ± 8.6 | 16.3 ± 7.1 | 28.0 ± 4.8 | 79.7 ± 9.2 | 1.61 ± 0.36 |
| cv | 14.0 | 19.3 | 43.8 | 17.1 | 11.6 | 22.2 |
| | dosage: 2 mg/10 ml whole blood culture | | | | | |
| n | 12 | 11 | 10 | 12 | 11 | 11 |
| $\overline{M} \pm s$ | 70.1 ± 9.2 | 48.8 ± 10.7 | 17.9 ± 10.5 | 35.1 ± 11.7 | 80.6 ± 11.5 | 1.44 ± 0.44 |
| cv | 13.1 | 21.9 | 58.5 | 33.4 | 14.3 | 30.9 |
| n | 12 | 11 | 10 | 12 | 11 | 11 |
| $\overline{\text{Diff}} \pm s$ | +2.37 ± 6.05 | +4.2 ± 5.5 | 15.7 ± 8.8 | +7.1 ± 11.9 | +0.93 ± 6.8 | −0.17 ± 0.43 |
| cv | 255 | 130 | 55.8 | 167 | 735 | 245 |
| n | 12 | 11 | 10 | 12 | 11 | 11 |
| $\overline{V} \pm s$ | 103.9 ± 9.5 | 109.7 ± 12.0 | 112.0 ± 58.1 | 127.4 ± 44.6 | 101.1 ± 8.4 | 90.3 ± 22.0 |
| cv | 9.1 | 10.9 | 51.9 | 35.0 | 8.3 | 24.4 |

TABLE 8

Qualitative evaluation of selected donors, which have been found by cytometry-determinations to be anomalous responders with respect to the shift of the OKT-8-positive T-subgroup after incubation of the whole blood cultures with thymus preparations.

| Donor | E Z. 2[a] | E Z. 4 | E Z. 6 | A 2 | B 2 | C 2 |
|---|---|---|---|---|---|---|
| GB$_1$ | +++[b] | +++ | +++ | − | − | − |
| GB$_2$ | 0[c] | 0 | 0 | 0 | 0 | 0 |
| BB$_1$ | + | − | − | 1 mg +[e] (119) 8 mg +[f] (116) 12 mg + +[g] (121) | 0 | ND |
| BB$_2$ | 0 | 0 | 0 | + | 0 | − |
| BB$_4$ | + | − | − | ++ | ++ | − |
| BB$_5$ | − | − | − | − | − | +++ |
| BP$_3$ | ++ | − | − | + | −(!) | 0 |
| WL$_1$ | ++ | − | − | ++ | 0 | ++ |
| WL$_2$ | ++ | − | − | ++ | 0 | +++ |
| UF$_1$ | +++++ | ++++ | +++++ | − | − | − |
| GZ$_1$ | − | − | − | ++ | ++ | ++++ |
| HIG$_2$ | ++ | − | − | +++ | ++ | ++ |
| RB$_1$ | ++ | − | − | ++ | 0 | ND |
| RL | − | − | − | + | 0 | 0 |

EZ = composition according to the present invention
A = peptide fraction from EZ; B = yellow substance from EZ; C = thymosin-fraction No. 5;
[a]dosage/10 ml whole blood culture
[b]qualitative evaluation: + 110–119%, ++ 120–149%, +++ 150–200%, ++++ 201–250%, +++++ 250%, -decrease under 80% of the value for OKT-8 positive T-cell subgroups of the corresponding control culture, which amounts to 100%.
[c]A significant effect; dosage:
[d]4 mg,
[e]1 mg,
[f]8 mg,
[g]12 mg.

(f) Evaluation:

The marking of the T-lymphocytes directly in whole blood (O) influences the range of scatter of the measured data, expressed as coefficient of variation (CV), insignificantly.

But the high range of scatter of the measured data, which are based on the marking with OKT-6 (specific for immature thymocytes) is remarkable. Here the CV is in the range of from 40 to 100%. If the quality of the marking with OKT-sera is judged by means of the ranges of scatter, respectively, then the series of increasing CV results in OKT-11 (specific for E-receptor on T-cells) <OKT-3 (specific for all T-cells) <OKT-4 (specific for T-helper cells) <OKT-8 (specific for T-suppressor cells). For unmodified cells (control cultures) the range of scatter is in the range of 7 to 20%, for cells of cultures with the addition of active ingredients it is some times the doubled value.

The same test persons show, when applying the same cell marking method and the same batches, on specific OKT-sera significant deviations from the measured value if the blood is taken at different days. But these deviations, which are related to the test persons, are within the range of scatter, which shows each T-cell type within the total measuring series, as the mean value for all test persons. Reliable values for the statistics can be obtained on the basis of mean ratios $\overline{M}_v$ (%) of the measured values with respect to the control values (100%), the corresponding standard deviations (S) and the ranges of scatter (CV %) derived therefrom.

When using the composition according to the present invention the most distinctive effect is seen in the increase of the OKT-8-positive cells, especially at a direct marking after isolation of the T-cells ($\overline{M}_v = 131.8\%$ of the control values) already at a concentration of 2 mg/10 ml culture batch. This very significant activity of the preparation according to the present invention which is in the direction of an increase of T-suppressor cells (cytotoxic subpopulation) remains also statistically significant ($\overline{M}_v = 120\%$), if the mean value is evaluated over all test persons (n = 21) and both methods of the T-cell marking (directly in whole blood or after isolation). The quotient of OKT-4/OKT-8 measured values, obtained on blood samples of healthy donors without any influence of active ingredients, normally has the value 1.5; deviations from this value clearly demonstrate a shift of the immunologic balance.

It has been found, that the composition according to the present invention is, with respect to the increase of OKT-8-positive T-suppressor cells (cytotoxic subpopulation) in its activity in the whole blood culture better than the thymosinfraction No. 5 ($\overline{M}_v$ 127%). The peptide fraction as a partial component of the preparation according to the invention shows an action pattern with respect to the T-cell-subpopulations, which is similar to the preparation, whereas the other component of the preparation, the yellow fraction, although it has a measurable influence on the whole blood culture, shows, that this influence is not significant with respect to any T-cell type. Therefore this component is significant as a synergistic acting additive, which increases the in-vitro-activity of the preparation significantly with respect to other thymus-preparations, as for instance thymosinfraction No. 5.

If in the above stated evaluation such test persons are eliminated, which, in the control cultures, show a OKT-4/OKT-8-ratio which is anomalous ($\neq 1.5$), then for the final assessment of the preparation on the basis of 17 measurements (n) a mean ratio OKT-8-positive cells to control group of 150% is obtained, with a range of scatter of only 16%. This is a very relevant result, because the range of scatter is within the normal limit value, which can be found in control cultures of blood of healthy test persons, as a mean value over all parameters of determination, both with direct marking in whole blood, and also with isolated T-cells.

In the in-vitro system (whole blood culture) a significant effect has been found with respect to the pronouncement of surface characteristics, which are typically for subpopulations of T-lymphocytes, and which have been detected by flow cytometry with monoclonal antibodies. Especially an increase of the characteristics has been found, which are characteristically for "suppressor"- and "cytotoxic"-T-cells, respectively, (OKT 8-positive cells). This effect has been greater with respect to some individuals (designated as "responder"), but also in the statistics, when compared with the reference substance "thymosin fraction No. 5".

All (healthy) test persons showed a profile of total stock of T-lymphocytes (eventually occuring lower values can depend on not noticed (latent) infections, which result in an increase of B-lymphocytes) and especially of helper (OKT 4-positive) and "suppressor"-/cytotoxic (OKT 8-positive) T-cells, which can be specified as "normal".

From the obtained results a clinical application of the preparation according to the present invention can be seen with patients, which have an anomalous stock of subpopulations, especially of "suppressor"-/cytotoxic (OKT 8-positive) cells. Such a condition is especially known for some connective tissue diseases, which are described as auto-immune diseases, in which almost without exception, a decrease of the OKT 8-positive subpopulation is present (rheumatoid arthritis, Lupus erythematodes, sclerodermatitis, Sjögren-syndrome, etc.). In this cases also in the "in-vitro"-system an even more significant effect can be expected on the increase of the number of OKT 8-positive cells; thereby it should also be possible to reduce the dosage of the active ingredient. When applying the preparation to patients of the described rheumatic types, before and during the application the cellular immune status has to be examined on peripheral lymphocytes with OKT-sera.

The type and amount of the application of the preparation according to the present invention depends especially on the kind and severity of the disease, and on the general condition and the sensitivity of the patient.

I claim:

1. A pharmaceutical composition useful in immunostimulation and immunoregulation said composition being extracted from mammalian thymus gland by means of a protease extraction of the thymus gland followed by a phenolic extraction which is then followed, after discharging the aqueous phase, by an ethanolic extraction of the remaining phenol phase producing a precipitate and a filtrate supernatant and comprising a first fraction obtained from the filtrate supernatant of the ethanolic extraction of mammalian thymus gland wherein said first fraction is yellow and enriched in riboflavin wherein said riboflavin is associated with thymus peptide and wherein said first yellow fraction is subject to chromatographic separation to obtain a further enriched yellow fraction, and a second peptide fraction from the thymus gland obtained from the precipitate of the ethanolic extract which fraction contains at least one of the group consisting of low molecular weight peptides wherein said peptides have a molecular weight of less than 2000 daltons, and wherein said second peptide fraction contains at least 75 percent by weight of hydrolyzable amino acids consisting of cysteine sulfonic acid, aspartic acid, threonine, serine, glutamic acid, proline, glycine, alanine, valine, isoleucine. leucine, tyrosine, phenylalanine, lysine, histidine, and arginine, and a pharmaceutically acceptable carrier.

2. Composition of claim 1, wherein said first fraction is obtained via chromatographic separation.

3. Composition of claim 2, wherein said chromatographic separation takes place on a column which contains aluminum oxide wherein water is used as eluent.

4. Composition of claim 1, wherein said hydrolyzable amino acids comprise about 3–5% by weight cysteine, about 8–10% by weight asparagine, about 3–5% by weight threonine, about 3–5% by weight serine, about 8–10% by weight glutamic acid, about 10–12% by weight proline, about 10–12% by weight glycine, about 4–6% by weight alanine, about 4–6% by weight valine, about 3–5% by weight isoleucine, about 4–6% by weight leucine, about 2–3% by weight tyrosine, about 3–5% by weight phenylalanine, about 4–6% by weight lysine, about 2–3% by weight histidine, and about 6–8% by weight arginine.

5. Composition as in claim 1, wherein said riboflavin rich fraction is characterized by a yellow color and contains about 50–55% by weight carbon, about 5–7% by weight hydrogen, and about 14–16% by weight nitrogen.

6. Composition as in claim 1, wherein said riboflavin rich fraction contains about 2–3% by weight of free amino acids.

7. Composition as in claim 1, wherein said riboflavin rich fraction contains cysteine sulfonic acid, asparagine threonine, serine, glutamine, proline, glycine, alanine, valine, methionine, isoleucine, leucine, tyrosine, phenylalanine, lysine, and arginine.

8. Composition of claim 1, wherein said composition comprises about 10.00 mg/ml of said first and second fractions, about 4.55 mg/ml phenol, about 5.00 mg/ml NaCl. and water to bring said composition to 1 ml.

9. Method of immunostimulation or immunoregulation of a subject comprising adminstering to said subject an immunostimulatory or immunoregulatory effective amount of the composition of claim 1.

10. Method of claim 9, wherein said immunostimulation or immunoregulation comprises increased production of T4 helper cells.

11. Method of claim 9, wherein said immunostimulation or immunoregulation comprises increased production of T8 cytotoxic T cells.

12. Method of treating autoimmune disease which comprises adminstering to a subject with an autoimmune disease an effective amount of the composition of claim 1.

13. Method of claim 12, wherein said disease is a connective tissue disease.

14. Method of claim 13, wherein said disease is rheumatoid arthritis.

15. Method of claim 13, wherein said disease is *Lupus erythematosis*.

16. Method of claim 13, wherein said disease is sclerodermatitis.

17. Method of claim 13, wherein said disease is sjogren syndrome.

* * * * *

UNITED STATES PATENT AND TRADEMARK OFFICE
CERTIFICATE OF CORRECTION

PATENT NO. : 4,826,680
DATED : May 2, 1989
INVENTOR(S) : Karl-Heinz Jaeger

It is certified that error appears in the above-identified patent and that said Letters Patent is hereby corrected as shown below:

| | |
|---|---|
| Col. 1, line 30: | change "977" to -- 1977 --. |
| Col. 1, line 47: | change "DE-OS 1 00 974" to -- DE-OS 31 00 974". |
| Col. 3, lines 15-16: | change "bacterial" to -- bacterially --. |
| Col. 4, lines 9-10: | change "at stirring with a" to -- with stirring at a --. |
| Col. 4, line 64: | change "oliquot" to -- aliquot --. |
| Col. 5, line 2: | change "glycin" to -- glycine --. |
| Col. 5, line 5: | change "0,797" to -- 0.797 --; and change "17,55" to -- 17.55 --. |
| Col. 5, line 21: | change "36,34" to -- 36.34 -- and change "8,8" to -- 8.8 --. |
| Col. 5, line 38: | change "12,5" to -- 12.5 --. |

UNITED STATES PATENT AND TRADEMARK OFFICE
CERTIFICATE OF CORRECTION

PATENT NO.  : 4,826,680
DATED       : May 2, 1989
INVENTOR(S) : Karl-Heinz Jaeger It is certified that error appears in the above-identified patent and that said Letters Patent is hereby corrected as shown below:

| | |
|---|---|
| Col. 11, line 9: | change "weight" to -- weights --. |
| Col. 16, line 20: | change "denatrated" to -- denaturated --. |
| Col. 18, line 53: | under col. 4, change "349" to -- 34.9 --. |
| Col. 19, line 44 entry "$RL_1$": | under column "4/8", change "0.10" to -- +0.14 --. |
| Col. 30, line 20: | change "sjogren" to -- Sjogren --. |

Signed and Sealed this

Seventeenth Day of July, 1990

Attest:

HARRY F. MANBECK, JR.

Attesting Officer

Commissioner of Patents and Trademarks